US008877756B2

(12) United States Patent
Dollinger et al.

(10) Patent No.: US 8,877,756 B2
(45) Date of Patent: Nov. 4, 2014

(54) SUBSTITUTED PTERIDINES

(75) Inventors: Horst Dollinger, Schemmerhoffen (DE); Domnic Martyres, Biberach (DE); Juergen Mack, Biberach (DE); Rolf Goeggel, Ulm (DE); Birgit Jung, Laupheim (DE); Peter Nickolaus, Warthausen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 12/689,273

(22) Filed: Jan. 19, 2010

(65) Prior Publication Data
US 2010/0120766 A1 May 13, 2010

Related U.S. Application Data

(62) Division of application No. 11/751,917, filed on May 22, 2007, now Pat. No. 7,674,788.

(30) Foreign Application Priority Data

May 24, 2006 (EP) .................................... 06114538

(51) Int. Cl.
| | |
|---|---|
| A61K 31/5025 | (2006.01) |
| C07D 519/00 | (2006.01) |
| C07D 475/08 | (2006.01) |
| A61P 29/00 | (2006.01) |
| A61P 1/00 | (2006.01) |
| A61P 35/00 | (2006.01) |

(52) U.S. Cl.
CPC ............ *C07D 475/08* (2013.01); *C07D 519/00* (2013.01)
USPC .................................... 514/249; 514/255.05

(58) Field of Classification Search
USPC ............................................ 514/255.05, 249
See application file for complete search history.

(56) References Cited

FOREIGN PATENT DOCUMENTS

| | | |
|---|---|---|
| CA | 1233179 A1 | 2/1988 |
| CA | 1337813 C | 12/1995 |
| CA | 2587266 A1 | 6/2006 |
| CA | 2653117 A1 | 11/2007 |
| CA | 2670155 A1 | 5/2008 |
| DE | 3540952 A1 | 5/1987 |
| EP | 0134922 A1 | 3/1985 |
| EP | 1225173 A1 | 7/2002 |
| JP | 6025991 | 2/1988 |
| JP | 2009511465 A | 3/2009 |
| JP | 2009537590 A | 10/2009 |
| WO | 0130779 A1 | 5/2001 |
| WO | 03062240 A1 | 7/2003 |
| WO | 2004056823 A1 | 7/2004 |
| WO | 2006056607 A1 | 6/2006 |
| WO | 2006058867 A2 | 6/2006 |
| WO | 2006058868 A2 | 6/2006 |
| WO | 2006058869 A2 | 6/2006 |
| WO | 2007135027 A1 | 11/2007 |
| WO | 2008061874 A2 | 5/2008 |

OTHER PUBLICATIONS

Walker, MedPage Today, Apr. 5, 2010, downloaded Oct. 23, 2010, http://www.medpagetoday.com/Pulmonology/SmokingCOPD/19393.*
Prehn, et al., J. Clin. Immunol., vol. 21, No. 5, 2002.*
Burgin, et al., Natur Biotechnol. vol. 28, #1, Jan. 2010.*
Tang, et al., Int'n'tl. Immunopharmacol. 10 (2010), 406-411.*
Wikipedia, Roflumilast, http://en.wikipedia.org/wiki/Roflumilast, downloaded Nov. 12, 2010.*
Banner, Katharine, H., et al; PDE4 Inhibition: A novel Approach for the Treatment of Inflammatory Bowel Disease; TRENDS in Pharmaceutical Sciences (2004) vol. 25, No. 8 pp. 430-436.
Huang, Zheng, et al; The Next Generation of PDE4 Inhibitors; Current Opinion in Chemical Biology (2001) vol. 5 pp. 432-438.
Spina, Domenico; The potential of PDE4 Inhibitors in Asthma or COPD; Current Opinion in Investigational Drugs (2000) vol. 1, No. 2 pp. 204-213.
Vignola, Antonio, Maurizio; PDE4 Inhibitors in COPD—A More Selective Approach to Treatment; respiratory Medicine (2004) vol. 98 pp. 495-503.
Spina, Domenico; PDE4 Inhibitors: Current Status; British Journal of Pharmacology (2008) vol. 155 pp. 308-315.
Huennemayer et al; J. Allergy and Clin. Immun (2004) vol. 113, Issue 2, Supplement, p. S222 and Abstract 786.
Griesser, Chapter 8, "The Importance of Solvates", 2006, p. 211-230. in the text, Polymorphism: In the Pharmaceutical Industry, Hilfiker.
Marko, et al., "Intracellular localization of 7-benzylamino-6-chloro-2-piperazino-4-pyrrolidino-pteridine in membrane structures impeding the inhibition of cytosolic cyclic AMP-specific phosphodiesterase", Biochemical Pharmacology, 2002, v. 63(4), p. 669-676.
Walker, MedPage Today, 2010, downloaded Oct. 23, 2010. Http://www.medpagetoday.com/Pulmonology/SmokingCOPD/19393.
Prehn, et al., "Potent Inhibition of Cytokine Production from Intestinlal Lamina Propria T Cells by Phosphodieterase-4 Inhibitory Thalidomide Analogues", Journal of Clinical Immunology, 2002, v. 21, No. 5.
Burgin, et al., "Design of phosphodieterase 4D (PDE4D) allosteric modulators for enhancing cognition with improved safety", Nature Biotechnology, 2010, v. 28, No. 1.
Tang, et al., "Action of a Novel PDE4 inhibitor ZL-n-91 on lipopolysaccharide-induced acute lung injury", International Immunopharmacology, 2010, v. 10, p. 406-411.
Wikipedia, Roflumilast, Http://en.wikipedia.org/wiki/Roflumilast, downloaded Nov. 10, 2010.

(Continued)

*Primary Examiner* — James O Wilson
*Assistant Examiner* — Cecilia M Jaisle
(74) *Attorney, Agent, or Firm* — Michael P. Morris; Timothy X. Witkowski

(57) ABSTRACT

The invention relates to new pteridines which are suitable for treating respiratory or gastrointestinal complaints or diseases, inflammatory diseases of the joints, skin or eyes, diseases of the peripheral or central nervous system and cancers. This invention also relates to pharmaceutical compositions containing these compounds.

3 Claims, No Drawings

(56) References Cited

OTHER PUBLICATIONS

Huennemayer, et al., Journal of Allergy and Clinical Immunology, 2004, vol. 113, Issue 2, Supplement, pp. S222 and Abstract 786.

Spina, D., "PDE4 Inhibitors: Current Status" British Journal of Pharmacology, 2008, v. 155, p. 308-315.

Nycomed's Roflumilast Press Release dated Mar. 1, 2011.

Huang, Z., et al., "The Next Generation of PDE4 Inhibitors", Current Opinion in Chemicall Biology, 2001, v. 5, p. 432-438.

Banner, K., et al., "PDE4 inhibition: a novel approach for the treatment of inflammatory bowel disease", Trends in Pharmaceutical Sciences, 2004, v. 25, No. 8, p. 430-436.

Vignola, A., "PDE4 inhibitors in COPD—a more selective approach to treatment", Respiratory Medicine, 2004, v. 98, p. 495-503.

Spina, D., "The potential of PDE4 inhibitors in asthma or COPD", Current Opinion in investigational drugs, 2000, v. 1, No. 2, p. 204-213.

Merz, Karl-Heinz, et al; Synthesis of 7-Benzylamino-6-chloro-2-piperazino-4-pyrrolidinopteridine and Novel Derivatives Free of Positional Isomers. Potent Inhibitors of cAMP-Specific Phosphodiesterase and of Malignant Tumor Cell Growth; Journal of Medicinal Chemistry (1998) vol. 41, No. 24 pp. 4733-4743.

Shaunta, D'Martina, et al., Cilomilast: Orally Active Selecting Phosphodieterase-4 Inhibitor, Ann. Pharmacotherapy, 2006, vol. 40, No. 10, p. 1822-1828.

Powerpoint Presentation to FDA-ARIFLO (cilomilast) Tablets, 15 mg, Pulmonary-Allergy Drugs advisory Committee meeting (2003).

* cited by examiner

SUBSTITUTED PTERIDINES

RELATED APPLICATIONS

This application is a divisional of co-pending U.S. application Ser. No. 11/751,917, filed May 22, 2007, which claims priority to European application no. 06114538, filed May 24, 2006, each of which is hereby incorporated by reference in its entirety.

The invention relates to new pteridines which are suitable for treating respiratory or gastrointestinal complaints or diseases, inflammatory diseases of the joints, skin or eyes, diseases of the peripheral or central nervous system and cancers. This invention also relates to pharmaceutical compositions containing these compounds.

BACKGROUND OF THE INVENTION

Pteridines are known from the prior art as active substances with an antiproliferative activity. See, e.g., Merz et al., Journal of Medicinal Chemistry 1998, 41, 4733-4743 (the preparation of 7-benzylamino-6-chloro-2-piperazino-4-pyrrolidinopteridine and derivatives thereof which are free from positional isomers). It has been shown that the compounds prepared are able to inhibit the growth of tumour cells. DE 3540952 describes 2-piperazino-pteridines which are substituted in the 6 position by a halogen atom selected from among a fluorine, chlorine or bromine atom. It has been shown that these compounds were able to inhibit the activity of tumour cells and human thrombocytes in vitro. DE 3323932 discloses 2-piperazino-pteridines which carry a dialkylamino, piperidino, morpholino, thiomorpholino or 1-oxidothiomorpholino group in the 4 position. It has been shown that these compounds were able to inhibit the activity of tumour cells and human thrombocytes in vitro. DE 3445298 describes pteridines with a large number of different substituents in the 2, 4, 6 and 7 position, while compounds with a 2-piperazino group on the pteridine skeleton are suitable as inhibitors of tumour growth and also have antithrombotic and metastasis-inhibiting properties. U.S. Pat. No. 2,940,972 discloses tri- and tetrasubstituted pteridine derivatives, commenting in general terms that these pteridines have valuable pharmacological properties, namely coronary artery dilating, sedative, antipyretic and analgesic activities.

The phosphodiesterase 4 inhibitors from the prior art are known to trigger side effects such as nausea and vomiting (Doherty, 1999, Curr. Op. Chem. Biol., Aug. 3, (4):466-73). The substances mentioned in this invention preferably inhibit the B-isoenzymes of phosphodiesterase 4 and therefore, are preferred PDE4B-inhibitors particularly suitable for treating the above-mentioned diseases. These are unlike other PDE4-inhibitors, which preferably inhibit other PDE4-isoenzymes (e.g. isoenzymes A, C or D), because they do not trigger side effects of nausea and vomiting in an animal model (S. Murinus, Yamamoto K. et al., Physiol. Behav., 2004, Oct. 30, 83(1), 151-6).

The aim of the present invention is to provide new compounds which are suitable for the prevention or treatment of respiratory or gastrointestinal complaints or diseases, inflammatory diseases of the joints, skin or eyes, diseases of the peripheral or central nervous system, or cancers, particularly those compounds which are characterized by reduced side effects, particularly emesis and nausea.

DESCRIPTION OF THE INVENTION

Surprisingly it has now been found that pteridines of formula 1 are suitable for treating inflammatory diseases.

The present invention therefore relates to compounds of formula 1

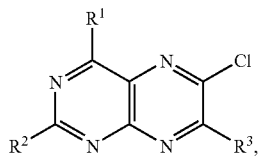

wherein
$R^1$ denotes a group selected from among a saturated or partially saturated four-, five-, six- or seven-membered heterocyclic group and may contain a five- or six-membered heteroaromatic group, which contains a nitrogen atom and may optionally contain another atom selected from among nitrogen, sulphur and oxygen;
and
$R^2$ denotes a group selected from among a saturated or partially saturated five-, six- or seven-membered heterocyclic group and a five- or six-membered heteroaromatic group, which contains a nitrogen atom and may optionally contain another atom selected from among nitrogen, sulphur and oxygen;
and wherein
$R^3$ denotes $NR^{3.1}R^{3.2}$ or $OR^{3.1}$, wherein
$R^{3.1}$ and $R^{3.2}$ in each case independently of one another denote H or a group selected from among $C_{1-6}$-alkyl, mono- or polyvalent, branched or unbranched $C_{1-6}$-alkanol, $C_{1-6}$-haloalkyl, $C_{1-6}$-alkylene-O—$C_{1-2}$-alkyl, a mono- or bicyclic, saturated or partially saturated $C_{3-10}$-cycloalkyl, mono- or bicyclic $C_{6-10}$-aryl, mono- or bicyclic, saturated or partially saturated, four- to ten-membered heterocyclic group with 1 to 3 heteroatoms selected from S, N or O, and a mono- or bicyclic, five- to ten-membered heteroaromatic group with 1 to 4 heteroatoms selected from S, N or O, which may optionally be substituted by one or more groups selected from among OH, (halogen), $C_{1-6}$-alkyl, $C_{1-6}$-alkanol, ($C_{1-6}$-haloalkyl), $COOR^{3.3}$, O—$C_{1-6}$-alkyl, $C_{6-10}$-aryl, $C_{3-10}$-cycloalkyl, four- to ten-membered heterocyclic group, five- to ten-membered heteroaromatic group and O—$C_{1-4}$-alkyl-phenyl, while this group may in turn optionally be substituted by at least one group selected from among halogen, OH, $C_{1-3}$-alkyl, $C_{1-3}$-haloalkyl,
and wherein
$R^{3.3}$ denotes H, $C_{1-6}$-alkyl or ($C_{1-6}$-alkanol),
or wherein
$R^3$ denotes a saturated or partially saturated four-, five-, six- or seven-membered heterocyclic group which contains a nitrogen atom and may optionally contain one or two other atoms selected from among nitrogen, sulphur and oxygen
and
which may optionally be substituted by one or more groups selected from among OH, halogen, $C_{1-6}$-alkyl, $C_{1-6}$-alkanol, $C_{1-4}$-alkyl-O—$C_{1-3}$-alkyl, $C_{6-10}$-aryl, $C_{3-10}$-cycloalkyl, five- to ten-membered heteroaryl, four- to ten-membered heterocyclic group, which contains a nitrogen atom and may optionally contain 1 or 2 further heteroatoms selected from N, S or O, $C_{1-2}$-alkylene-$C_{5-10}$-heteroaryl and $C_{1-2}$-alkylene-$C_{4-10}$ heterocycle, which contains a nitrogen atom and may optionally contain 1 or 2 further heteroatoms selected from N, S or O, which may in turn optionally be substituted by one or more groups selected from among methyl, ethyl, O-methyl, Cl, F and OH, or wherein $R^3$ denotes a saturated or partially saturated, bi- or polycyclic seven-, eight-, nine- or ten-membered heterocyclic group, which contains a nitrogen atom and may optionally contain one, two or three other atoms selected from among nitrogen, sulphur and oxygen and which may optionally be substituted by one or more groups selected from among OH, halogen, $C_{1-6}$-alkyl, $C_{1-6}$-alkanol, $C_{1-4}$-alkylene-O—$C_{1-3}$-alkyl, $C_{6-10}$-aryl, $C_{3-10}$-cycloalkyl, five- to ten-membered heteroaryl, four- to ten-membered heterocyclic group, $C_{1-2}$-alkylene-$C_{5-10}$-heteroaryl and $C_{1-2}$-alkylene-$C_{4-10}$ heterocycle, which may in turn optionally be substituted by one or more groups selected from among methyl, ethyl, O-methyl, Cl, F and OH, and the pharmacologically acceptable salts, diastereomers, enantiomers, racemates, hydrates or solvates thereof.

Also particularly preferred are compounds of formula 1, wherein $R^1$ denotes a saturated or unsaturated four, five- or six-membered heterocyclic group or heteroaromatic group, which contains a nitrogen atom and may optionally contain another atom selected from among nitrogen, sulphur and oxygen;

and $R^2$ denotes a five-, six- or seven-membered heterocyclic group or heteroaromatic group which contains a nitrogen atom and may optionally contain another atom selected from among nitrogen, sulphur and oxygen;

and wherein $R^3$ denotes $NR^{3.1}R^{3.2}$ or $OR^{3.1}$, wherein $R^{3.1}$ and $R^{3.2}$ each independently of one another denote H or a group selected from among $C_{1-6}$-alkyl, mono- or polyvalent, branched or unbranched $C_{1-6}$-alkanol, $C_{1-6}$-haloalkyl, $C_{1-6}$-alkylene-O—$C_{1-2}$-alkyl, mono- or bicyclic, saturated or partially saturated $C_{3-10}$-cycloalkyl, phenyl, mono- or bicyclic, saturated or partially saturated, four- to ten-membered heterocyclic group with 1 or 2 heteroatoms selected from S, N or O, and a mono- or bicyclic, five- to ten-membered heteroaromatic group with 1, 2 or 3 heteroatoms selected from S, N or O, which may optionally be substituted by one or more groups selected from among OH, $C_{1-6}$-alkyl, $C_{1-6}$-alkanol, COO—$C_{1-3}$-alkyl, O—$C_{1-3}$-alkyl, phenyl, $C_{3-10}$-cycloalkyl, four- to ten-membered heterocyclic group, five- to ten-membered heteroaromatic group and O—$CH_2$-phenyl, while this group may in turn optionally be substituted by at least one group selected from among halogen, OH, $C_{1-3}$-alkyl, $C_{1-3}$-haloalkyl, or wherein $R^3$ denotes a saturated or partially saturated four-, five-, six- or seven-membered heterocyclic group, which contains a nitrogen atom and may optionally contain one or two other atoms selected from among nitrogen, sulphur and oxygen and which may optionally be substituted by one or more groups selected from among OH, $C_{1-6}$-alkyl, $C_{1-6}$-alkanol, $CH_2$—O—$CH_3$, phenyl, $C_{3-10}$-cycloalkyl, five- to ten-membered heteroaryl, four- to ten-membered heterocyclic group, which contains a nitrogen atom and may optionally contain 1 or 2 further heteroatoms selected from N, S or O, $CH_2$—$C_{5-10}$-heteroaryl and $CH_2$—$C_{4-10}$ heterocycle, which contains a nitrogen atom and may optionally contain 1 or 2 further heteroatoms selected from N, S or O, which may in turn optionally be substituted by one or more groups selected from among methyl, O-methyl, Cl and OH, or wherein $R^3$ denotes a saturated or partially saturated, bi- or polycyclic seven-, eight-, nine- or ten-membered heterocyclic group, which contains a nitrogen atom and which may optionally contain one, two or three other atoms selected from among nitrogen, sulphur and oxygen and which may optionally be substituted by one or more groups selected from among OH, $C_{1-6}$-alkyl, $C_{1-6}$-alkanol, $CH_2$—O—$CH_3$, phenyl, $C_{3-10}$-cycloalkyl, five- to ten-membered heteroaryl, four- to ten-membered heterocyclic group, $CH_2$—$C_{5-10}$-heteroaryl and $CH_2$—$C_{4-10}$ heterocycle, which may in turn optionally be substituted by one or more groups selected from among methyl, O-methyl, Cl and OH, and the pharmacologically acceptable salts, diastereomers, enantiomers, racemates, hydrates or solvates thereof.

Also particularly preferred are compounds of formula 1, wherein $R^1$ and $R^2$ have the meanings stated above and wherein $R^3$ denotes a saturated or partially saturated four-, five-, six- or seven-membered heterocyclic group which contains a nitrogen atom and is linked to the rest of the molecule via this nitrogen atom and which may optionally contain one or two other atoms selected from among nitrogen, sulphur and oxygen and which may optionally be substituted by one or more groups selected from among OH, (halogen), $C_{1-6}$-alkyl, $C_{1-6}$-alkanol, $C_{1-4}$-alkyl-O—$C_{1-3}$-alkyl, $C_{6-10}$-aryl, $C_{3-10}$-cycloalkyl, five- to ten-membered heteroaryl, four- to ten-membered heterocyclic group, which contains a nitrogen atom and may optionally contain 1 or 2 further heteroatoms selected from N, S or O, $C_{1-2}$-alkylene-$C_{5-10}$-heteroaryl and $C_{1-2}$-alkylene-$C_{4-10}$ heterocycle, which contains a nitrogen atom and may optionally contain 1 or 2 further heteroatoms selected from N, S or O, which may in turn optionally be substituted by one or more groups selected from among methyl, ethyl, O-methyl, Cl, F and OH, or wherein $R^3$ denotes a saturated or partially saturated, bi- or polycyclic seven-, eight-, nine- or ten-membered heterocyclic group, which contains a nitrogen atom and is linked to the rest of the molecule via this nitrogen atom and which may optionally contain one, two or three other atoms selected from among nitrogen, sulphur and oxygen and which may optionally be substituted by one or more groups selected from among OH, (halogen), $C_{1-6}$-alkyl, $C_{1-6}$-alkanol, $C_{1-4}$-alkyl-O—$C_{1-3}$-alkyl, $C_{6-10}$-aryl, $C_{3-10}$-cycloalkyl, five- to ten-membered heteroaryl, four- to ten-membered heterocyclic group, $C_{1-2}$-alkylene-$C_{5-10}$-heteroaryl and $C_{1-2}$-alkylene-$C_{4-10}$ heterocycle, which may in turn optionally be substituted by one or more groups selected from among methyl, ethyl, O-methyl, Cl, F and OH, and pharmacologically acceptable salts, diastereomers, enantiomers, racemates, hydrates or solvates thereof.

Also particularly preferred are compounds of formula 1, wherein
R¹ denotes pyrrolidine or azetidine and the pharmacologically acceptable salts, diastereomers, enantiomers, racemates, hydrates or solvates thereof.

Also particularly preferred are compounds of formula 1, wherein
R¹ and R³ and $R^{3.1}$, $R^{3.2}$ and $R^{3.3}$ have the meanings stated above
and wherein
R² denotes piperazine and the pharmacologically acceptable salts, diastereomers, enantiomers, racemates, hydrates or solvates thereof.

Also particularly preferred are compounds of formula 1, wherein
R¹, R² and $R^{3.1}$ have the meanings stated above
and wherein
R³ denotes $NHR^{3.1}$,
as well as pharmacologically acceptable salts, diastereomers, enantiomers, racemates, hydrates or solvates thereof.

Also particularly preferred are compounds of formula 1, wherein
R¹ and R² have the meanings stated above
wherein
R³ denotes $NHR^{3.2}$,
and wherein
$R^{3.2}$ denotes a branched or unbranched, mono- or polyvalent $C_{1-6}$-alkanol or a $C_{3-6}$-cycloalkyl
and the pharmacologically acceptable salts, diastereomers, enantiomers, racemates, hydrates or solvates thereof.

Also particularly preferred are compounds of formula 1, wherein
R³ denotes $NHR^{3.1}$ or $OR^{3.1}$
$R^{3.1}$ denotes a saturated or unsaturated, five- or six-membered heterocyclic group with 1 or 2 heteroatoms selected independently of one another from among O, S and N,
which may optionally be substituted by one of the groups selected from among OH, methyl, ethyl, a branched or unbranched $C_{1-4}$-alkanol, phenyl, $C_{3-10}$-cycloalkyl.

Also particularly preferred are the above compounds of formula 1, wherein
R³ denotes $NHR^{3.1}$ or $OR^{3.1}$ and
$R^{3.1}$ is tetrahydrofuryl or tetrahydropyranyl,
which may optionally be substituted by one of the groups selected from among OH, methyl, ethyl, a branched or unbranched $C_{1-4}$-alkanol, phenyl, $C_{3-10}$-cycloalkyl.

Also particularly preferred are compounds of formula 1, wherein
R¹ and R² have the meanings stated above,
and wherein
R³ denotes a group selected from among a saturated five- or six-membered heterocyclic group and a bicyclic saturated or partially saturated eight-, nine- or ten-membered heterocyclic group which contains a nitrogen atom and is linked to the rest of the molecule via this nitrogen atom and which may optionally contain another atom selected from among nitrogen, sulphur and oxygen and which may optionally be substituted by one or more groups selected from among OH, methyl, ethyl, a branched or unbranched $C_{1-4}$-alkanol, phenyl, $C_{3-10}$-cycloalkyl, a five- to ten-membered heteroaryl and a four- to ten-membered heterocyclic group,
as well as pharmacologically acceptable salts, diastereomers, enantiomers, racemates, hydrates or solvates thereof.

Also particularly preferred are compounds of formula 1, wherein
R¹ and R² have the meanings stated above,
and wherein
R³ denotes pyrrolidine, which is linked to the rest of the molecule via the nitrogen atom and which may optionally be substituted by one or more groups selected from among OH, methyl, ethyl and a branched or unbranched $C_{1-4}$-alkanol,
and pharmacologically acceptable salts, diastereomers, enantiomers, racemates, hydrates or solvates thereof.

Also particularly preferred are compounds of formula 1, wherein
R¹ denotes

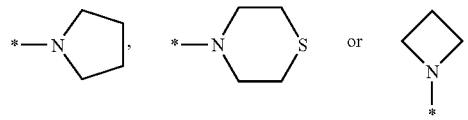

and
R² denotes

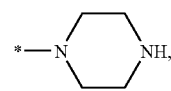

and
R³ denotes

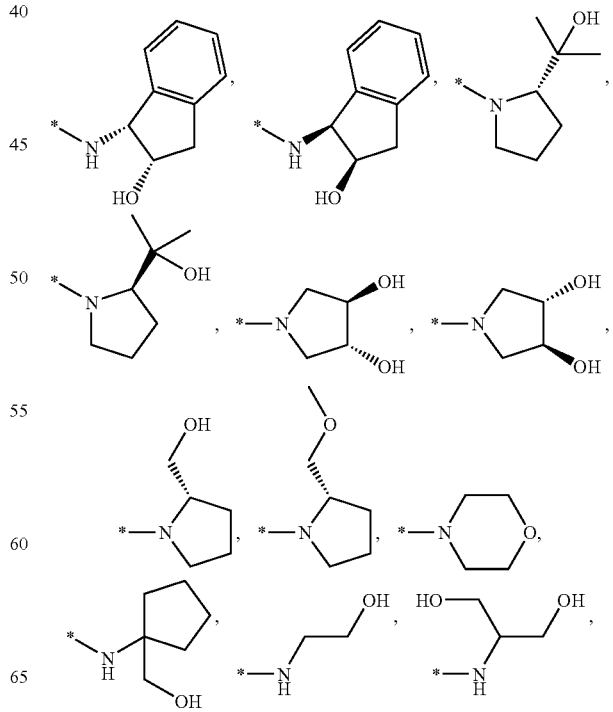

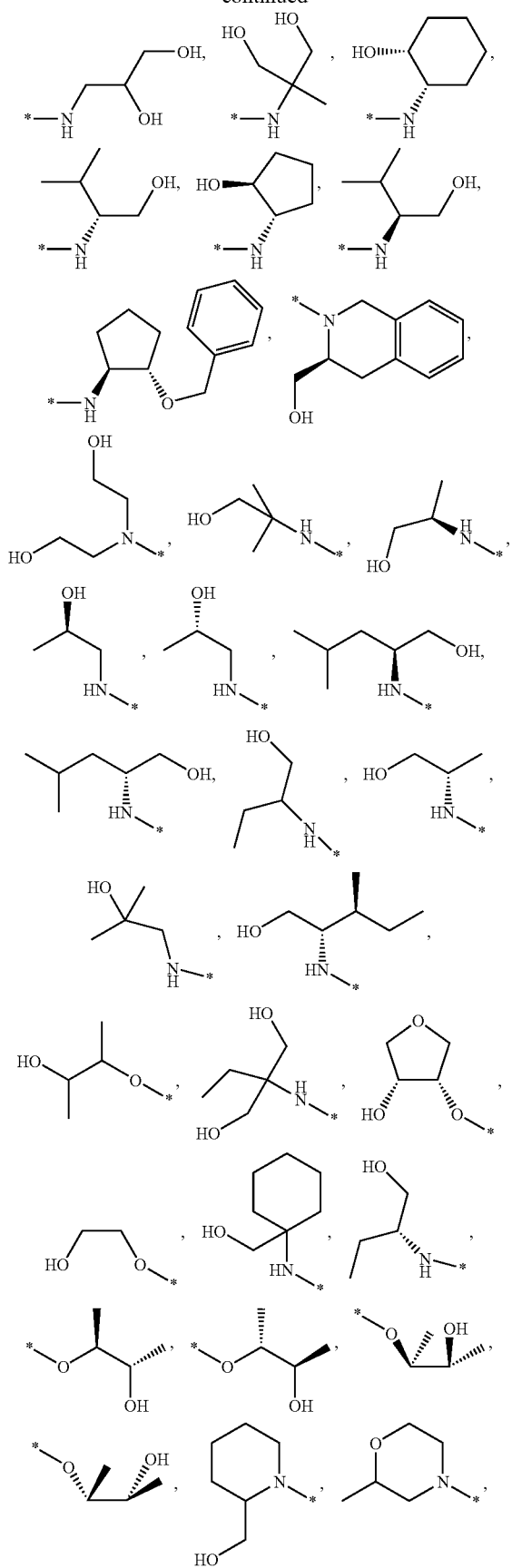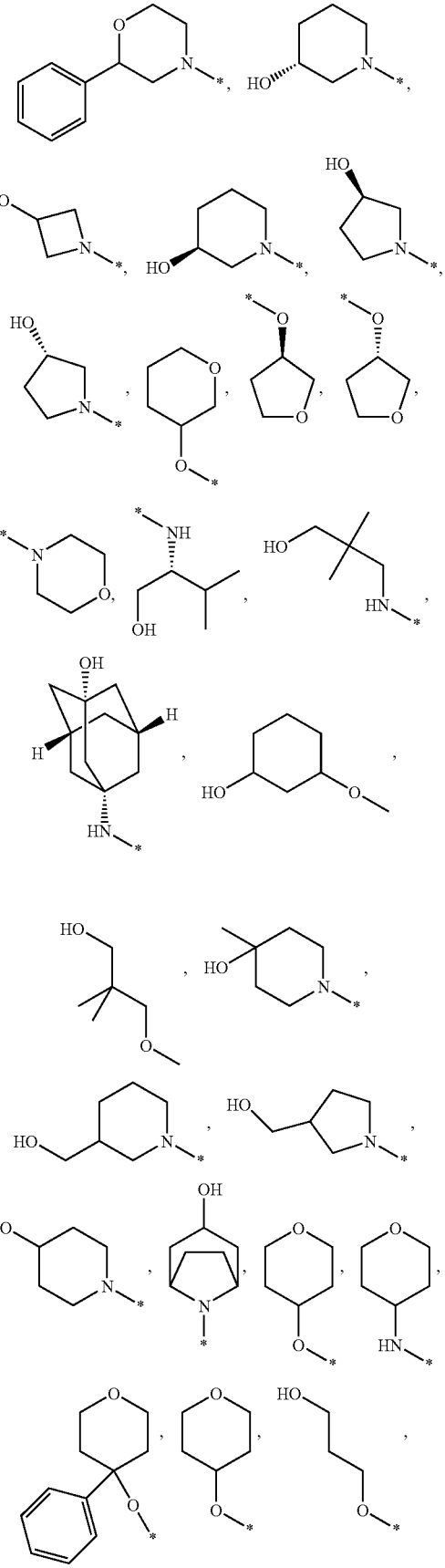

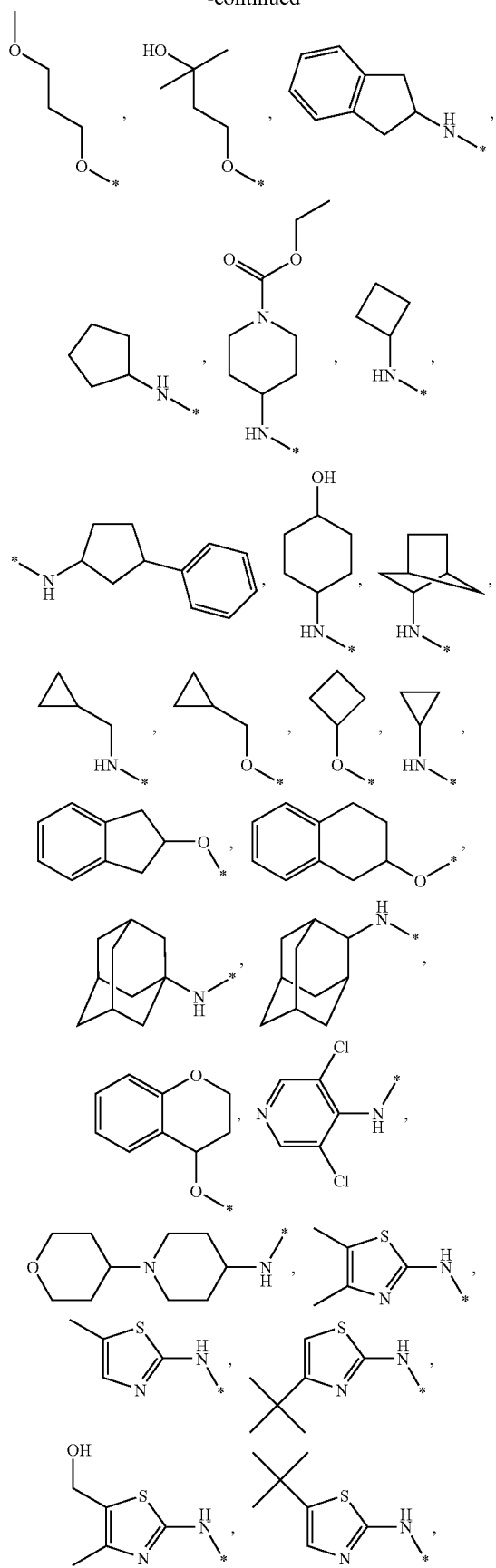
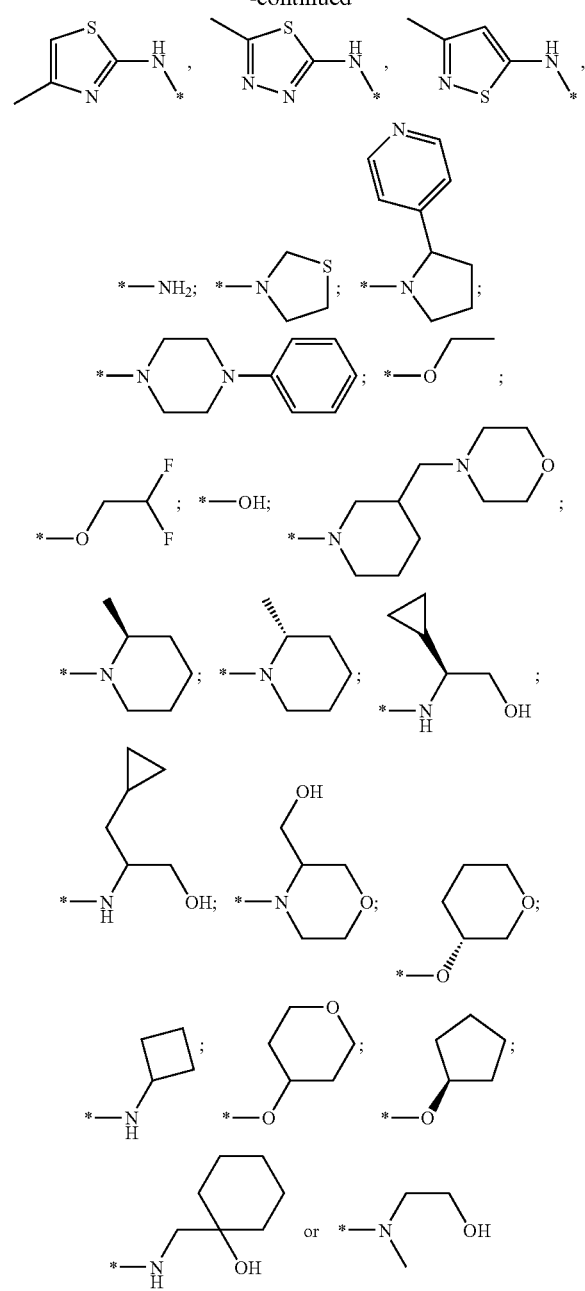
and the pharmacologically acceptable salts, diastereomers, enantiomers, racemates, hydrates or solvates thereof.
Also particularly preferred are compounds of formula 2,
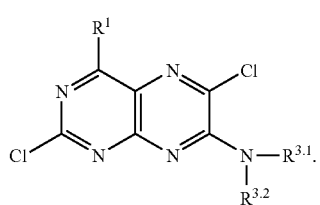

of formula 3

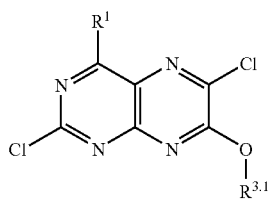

3 or of formula 4

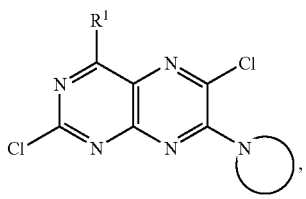

4 wherein $R^{3.1}$ and $R^{3.2}$ have the meanings defined hereinbefore, wherein $R^1$ have the meanings defined hereinbefore, preferably have the meanings pyrrolidinyl, azetidinyl or thiomorpholinyl, and wherein

is selected from among a saturated or partially saturated four-, five-, six- or seven-membered monocyclic heterocyclic group or a seven- to ten-membered bicyclic heterocyclic group, which is linked to the rest of the molecule via a nitrogen atom and which may optionally contain one or two other atoms selected from among nitrogen, sulphur and oxygen and which may optionally be substituted by one or more groups selected from among OH, halogen, $C_{1-6}$-alkyl, $C_{1-6}$-alkanol, $C_{1-4}$-alkyl-O—$C_{1-3}$-alkyl, $C_{6-10}$-aryl, $C_{3-10}$-cycloalkyl, five- to ten-membered heteroaryl, four- to ten-membered heterocyclic group, $C_{1-2}$-alkylene-$C_{5-10}$-heteroaryl and $C_{1-2}$-alkylene-$C_{4-10}$ heterocycle, which may in turn optionally be substituted by one or more groups selected from among methyl, ethyl, O-methyl, Cl, F and OH, and pharmacologically acceptable salts, diastereomers, enantiomers, racemates, hydrates or solvates thereof. These compounds of formulae 2, 3 and 4 are intermediate products of the methods of preparing the compounds of formula 1 which are prepared according to reaction schemes 1, 2 or 3.

The invention also relates to the above-mentioned compounds of formula 1 for use as pharmaceutical compositions.

In another aspect the invention relates to the use of the above-mentioned compounds for preparing a medicament for the treatment of diseases which can be treated by inhibition of the PDE4 enzyme.

The above-mentioned compounds are preferably used to prepare a medicament for the treatment of respiratory diseases, gastrointestinal complaints, inflammatory diseases of the joints, skin or eyes, cancers, and diseases of the peripheral or central nervous system.

The above-mentioned compounds are particularly preferably used to prepare a medicament for the prevention and/or treatment of respiratory or pulmonary diseases which are accompanied by increased mucus production, inflammations and/or obstructive diseases of the respiratory tract.

It is also preferable to use the compounds as defined above to prepare a medicament for the treatment of inflammatory diseases of the gastrointestinal tract.

The invention relates in particular to the use of the compounds defined above for preparing a medicament for the treatment of inflammatory and/or obstructive diseases such as COPD, chronic sinusitis, asthma, Crohn's disease and ulcerative colitis.

It is also preferred to use the compounds as defined above to prepare a medicament for the prevention and/or treatment of diseases of the peripheral or central nervous system such as depression, bipolar or manic depression, acute and chronic anxiety states, schizophrenia, Alzheimer's disease, Parkinson's disease, acute and chronic multiple sclerosis or acute and chronic pain and brain damage caused by stroke, hypoxia or craniocerebral trauma.

It is also preferred to use the compounds as defined above to prepare a medicament for the treatment of cancers such as e.g. acute and chronic leukaemias, acute lymphatic leukaemia (ALL) and acute myeloid leukaemia (AML), chronic lymphatic leukaemia (CLL) and chronic myeloid leukaemia (CML), acute non-lymphocytic leukaemia (ANLL), hair cell leukaemia, acute promyelocytic leukaemia (APL), particularly the APL subform with a chromosomal t(15; 17) translocation, diseases of the lymphatic organs, Hodgkin's lymphomas and non-Hodgkin's lymphomas and bone tumours such as e.g. osteosarcoma and all kinds of gliomas such as e.g. oligodendroglioma and glioblastoma.

In the above uses of the pteridine compounds according to the invention for preparing a medicament for the prevention and/or treatment of the above-mentioned diseases as a rule the side effects of the treatment are reduced compared with known therapeutics according to the prior art.

In particular the emesis and nausea that frequently occur as undesirable side effects are reduced when using the compounds according to formula 1.

Terms and Definitions Used

Within the scope of this application, in the definition of possible substituents, these may also be represented in the form of a structural formula. An asterisk (*) in the structural formula of the substituent is to be understood as being the linking point to the rest of the molecule. Thus for example the groups N-piperidinyl (I), 4-piperidinyl (II), 2-tolyl (III), 3-tolyl (IV) and 4-tolyl (V) are shown as follows:

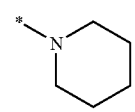

I

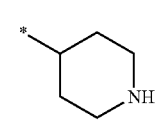

II

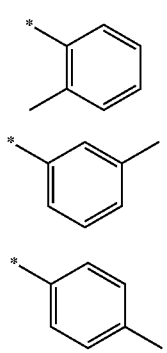

If there is no asterisk (*) in the structural formula of the substituent, each hydrogen atom may be removed at the substituent and the valency thus freed may serve as a binding site to the rest of a molecule. Thus, for example, VI may represent 2-tolyl, 3-tolyl, 4-tolyl and benzyl.

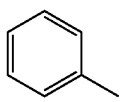

By pharmacologically acceptable acid addition salts are meant for example the salts which are selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate, preferably hydrochloride, hydrobromide, hydrosulphate, hydrophosphate, hydrofumarate and hydromethanesulphonate.

By the term "$C_{1-6}$-alkyl" (including those which are part of other groups) are meant branched and unbranched alkyl groups with 1 to 6 carbon atoms and by the term "$C_{1-4}$-alkyl" are meant branched and unbranched alkyl groups with 1 to 4 carbon atoms. Alkyl groups with 1 to 4 carbon atoms are preferred. Examples of these include: methyl, ethyl, n-propyl, iso-propyl, n-butyl, iso-butyl, sec-butyl, tert-butyl, n-pentyl, iso-pentyl, neo-pentyl or hexyl. The abbreviations Me, Et, n-Pr, i-Pr, n-Bu, i-Bu, t-Bu, etc. may also optionally be used for the above-mentioned groups. Unless stated otherwise, the definitions propyl, butyl, pentyl and hexyl include all the possible isomeric forms of the groups in question. Thus, for example, propyl includes n-propyl and iso-propyl, butyl includes iso-butyl, sec-butyl and tert-butyl etc.

By the term "$C_{1-6}$-alkanol" (including those which are part of other groups) are meant branched and unbranched alkyl groups with 1 to 6 carbon atoms which are substituted by one or more hydroxyl groups and by the term "$C_{1-4}$-alkanol" are meant branched and unbranched alkyl groups with 1 to 4 carbon atoms which are substituted by one or more hydroxyl groups. $C_{1-6}$-alkanols which are substituted by a hydroxyl group are also referred to as "monovalent" $C_{1-6}$-alkanols. $C_{1-6}$-alkanols which are substituted by two or more hydroxyl groups are also referred to as "polyvalent" $C_{1-6}$-alkanols. Alkanol groups with 1 to 4 carbon atoms are preferred. Examples of these include: $CH_2$—OH, ethyl-OH, n-propyl-OH, n-butyl-OH, iso-propyl-OH, n-butyl-OH, iso-butyl-OH, sec-butyl-OH, ten-butyl-OH, n-pentyl-OH, iso-pentyl-OH, neo-pentyl-OH, hexyl-OH,

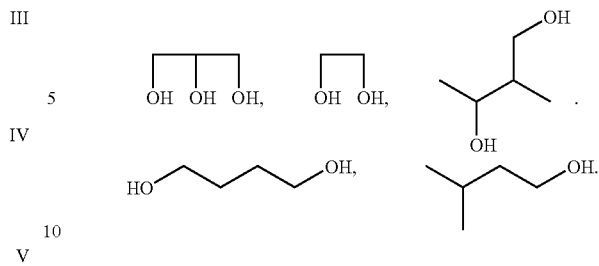

By the term "$C_{2-6}$-alkenyl" (including those which are part of other groups) are meant branched and unbranched alkenyl groups with 2 to 6 carbon atoms and by the term "$C_{2-4}$-alkenyl" are meant branched and unbranched alkenyl groups with 2 to 4 carbon atoms, provided that they have at least one double bond. Alkenyl groups with 2 to 4 carbon atoms are preferred. Examples of these include: ethenyl or vinyl, propenyl, butenyl, pentenyl or hexenyl. Unless stated otherwise, the definitions propenyl, butenyl, pentenyl and hexenyl include all the possible isomeric forms of the groups in question. Thus, for example, propenyl includes 1-propenyl and 2-propenyl, butenyl includes 1-, 2- and 3-butenyl, 1-methyl-1-propenyl, 1-methyl-2-propenyl etc.

By the term "$C_{2-6}$-alkynyl" (including those which are part of other groups) are meant branched and unbranched alkynyl groups with 2 to 6 carbon atoms and by the term "$C_{2-4}$-alkynyl" are meant branched and unbranched alkynyl groups with 2 to 4 carbon atoms, provided that they have at least one triple bond. Alkynyl groups with 2 to 4 carbon atoms are preferred. Examples of these include: ethynyl, propynyl, butynyl, pentynyl or hexynyl. Unless stated otherwise, the definitions propynyl, butynyl, pentynyl and hexynyl include all the possible isomeric forms of the groups in question. Thus, for example, propynyl includes 1-propynyl and 2-propynyl, butynyl includes 1,2- and 3-butynyl, 1-methyl-1-propynyl, 1-methyl-2-propynyl etc.

By the term "$C_{1-4}$-alkylene" or "$C_{1-6}$-alkylene (including those which are part of other groups) are meant branched and unbranched alkylene groups with 1 to 4 or 1 to 6 carbon atoms. Examples of these include: methylene, ethylene, propylene, 1-methylethylene, butylene, 1-methylpropylene, 1,1-dimethylethylene or 1,2-dimethylethylene. Unless stated otherwise, the definitions propylene and butylene include all the possible isomeric forms of the groups in question with the same number of carbons. Thus, for example, propyl also includes 1-methylethylene and butylene includes 1-methylpropylene, 1,1-dimethylethylene, 1,2-dimethylethylene. If the carbon chain is to be substituted by a group which together with one or two carbon atoms of the alkylene chain forms a carbocyclic ring with 3, 4, 5 or 6 carbon atoms, this includes, inter alia, the following examples of the rings:

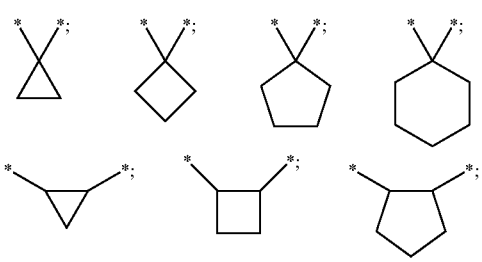

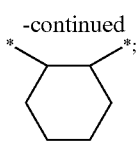

By the term "$C_{3-6}$-cycloalkyl" (including those which are part of other groups) are meant cyclic alkyl groups with 3 to 6 carbon atoms. Examples of these include: cyclopropyl, cyclobutyl, cyclopentyl or cyclohexyl. Unless otherwise stated, the cyclic alkyl groups may be substituted by one or more groups selected from among methyl, ethyl, iso-propyl, tert-butyl, hydroxy, fluorine, chlorine, bromine and iodine.

By the term "$C_{7-11}$-aralkyl" (including those which are part of other groups) are meant branched and unbranched alkyl groups with 1 to 5 carbon atoms which are substituted by an aromatic ring system with 6 carbon atoms. Examples of these include: benzyl, 1- or 2-phenylethyl. Unless stated otherwise, the aromatic groups may be substituted by one or more groups selected from among methyl, ethyl, iso-propyl, tert-butyl, hydroxy, fluorine, chlorine, bromine and iodine.

"Halogen" within the scope of the present invention denotes fluorine, chlorine, bromine or iodine. Unless stated to the contrary, fluorine, chlorine and bromine are regarded as preferred halogens.

By the term "$C_{1-6}$-haloalkyl" (including those which are part of other groups) are meant branched and unbranched alkyl groups with 1 to 6 carbon atoms, which are substituted by one or more halogen atoms. By the term "$C_{1-4}$-haloalkyl" are meant branched and unbranched alkyl groups with 1 to 4 carbon atoms, which are substituted by one or more halogen atoms. Alkyl groups with 1 to 4 carbon atoms are preferred. Examples of these include: $CF_3$, $CHF_2$, $CH_2F$, $CH_2CF_3$.

By the term "$C_{6-10}$-aryl" (including those which are part of other groups) are meant aromatic ring systems with 6 or 10 carbon atoms. Examples of these include: phenyl or naphthyl, the preferred aryl group being phenyl. Unless otherwise stated, the aromatic groups may be substituted by one or more groups selected from among methyl, ethyl, iso-propyl, tert-butyl, hydroxy, fluorine, chlorine, bromine and iodine.

By the term "heterocyclic rings" or "heterocyclic group" are meant four-, five-, six- or seven-membered, saturated, unsaturated or partially unsaturated monocyclic heterocyclic rings or seven-, eight-, nine- or ten-membered, heterocyclic rings which may contain one, two or three heteroatoms selected from among oxygen, sulphur and nitrogen. At the same time the ring may be linked to the molecule through a carbon atom or, if available, through a nitrogen atom. The following are examples of five-, six- or seven-membered, saturated, unsaturated or partially unsaturated heterocycles:

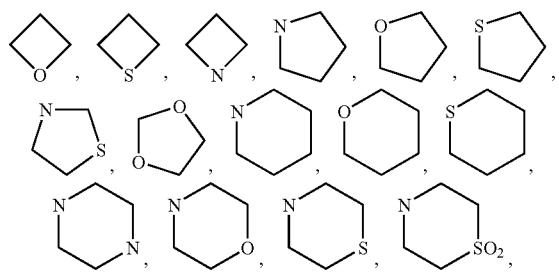

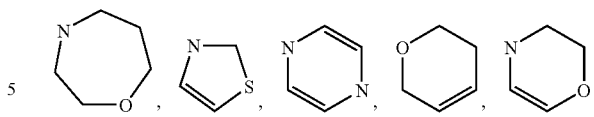

Unless otherwise mentioned, a heterocyclic ring may be provided with a keto group. Examples include.

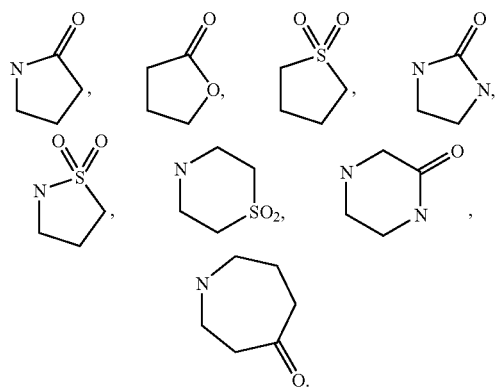

Examples of seven-, eight-, nine- or ten-membered saturated, unsaturated or partially unsaturated bicyclic heterocycles include pyrrolizine, indole, indolizine, isoindole, indazole, purine, quinoline, isoquinoline, benzimidazole, benzofuran, benzopyran, benzothiazole, benzoisothiazole, pyridopyrimidine, pteridine, pyrimidopyrimidine,

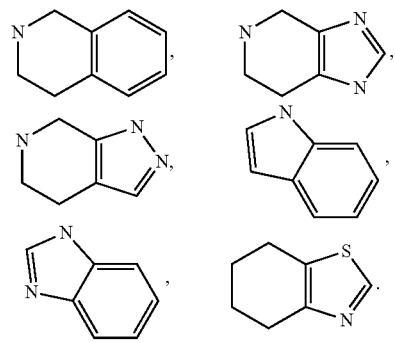

Although encompassed by the term "heterocyclic rings" or "heterocyclic group", the term "heteroaromatic group" or "heteroaryl" denotes five- or six-membered heterocyclic monocyclic aromatic groups or 5-10 membered, bicyclic heteroaryl rings which may contain one, two or three heteroatoms selected from among oxygen, sulphur and nitrogen, and sufficient conjugated double bonds to form an aromatic system. The ring may be linked to the molecule through a carbon atom or—if available—through a nitrogen atom. Examples of five- or six-membered heteroaryls include:

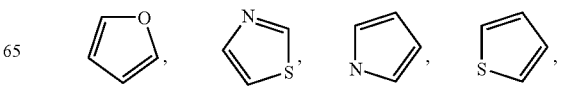

-continued

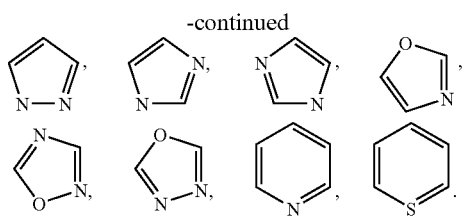

EXAMPLES

The compounds according to the invention may be prepared by methods known from the literature as described for example in DE 3540952.

The compounds according to the invention are prepared according to Schemes 1 to 3.

The following example compounds were prepared according to

Scheme 1:

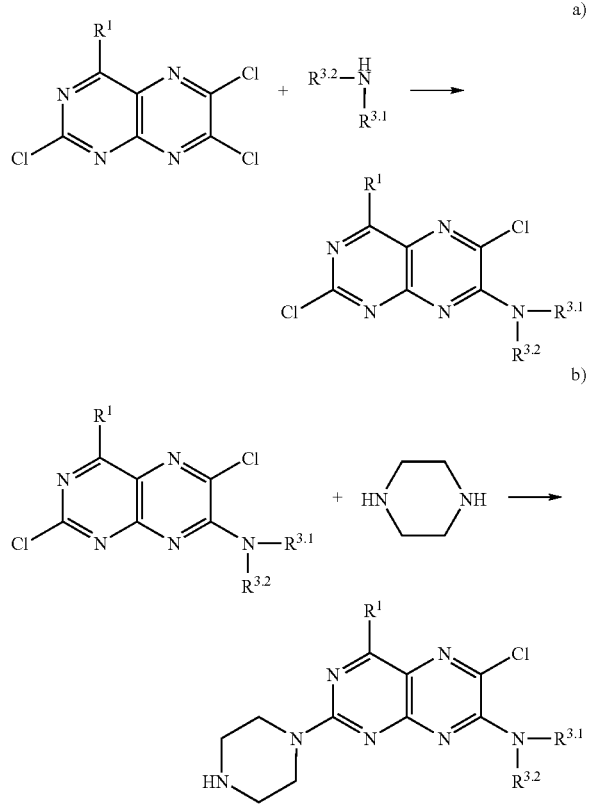

$R^1$ = 1-Pyrrolidinyl; 4-Thiomorpholinyl, 1-Azetidinyl

Example 1

7-amino-6-chloro-2-piperazin-1-yl-4-pyrrolidin-1-yl-pteridine (Example compound 99 from Table 1, prepared according to Scheme 1)

a) 7-amino-2,6-dichloro-4-pyrrolidin-1-yl-pteridine: 500 mg (1.6 mmol) 4-pyrrolidin-1-yl-2,6,7-trichloro-pteridine are combined with 10 ml dioxane and 15 ml of a 0.5 molar solution of ammonia in dioxane and stirred for approx. 16 h at 60° C. The mixture is mixed with water and extracted with dichloromethane. The organic phase is washed with water, dried on sodium sulphate and the solvent is eliminated in vacuo. The residue is used in the next step without further purification.

b) 7-amino-6-chloro-2-piperazin-1-yl-4-pyrrolidin-1-yl-pteridine: The residue from a) is dissolved in 15 ml dioxane and slowly added to a solution of 0.707 g (8 mmol) piperazine in 10 ml dioxane heated to 80° C. The mixture is stirred for another hour, then the mixture is mixed with water and extracted with dichloromethane. The organic phase is washed with water, dried on sodium sulphate and the solvent is eliminated in vacuo. The residue is purified by chromatography. Yield 410 mg (56% of theoretical).

Example 2

6-chloro-7-cyclobutylamino-2-piperazin-1-yl-4-pyrrolidin-1-yl-pteridine (Example compound 76 from Table 1, prepared according to Scheme 1)

a) 7-cyclobutylamino-2,6-dichloro-4-pyrrolidin-1-yl-pteridine: 250 mg (0.82 mmol) 4-pyrrolidin-1-yl-2,6,7-trichloro-pteridine are suspended in 25 ml of tetrahydrofuran and combined with 70 μl (0.82 mmol) cyclobutylamine and 175 μl (1 mmol) diisopropylethylamine. The mixture is stirred for approx. 16 h at ambient temperature, mixed with 20 ml of water and extracted twice with 20 ml dichloromethane. The organic phase is dried on sodium sulphate and the solvent is eliminated in vacuo. The residue is used in the next step without further purification.

b) 6-chloro-7-cyclobutylamino-2-piperazin-1-yl-4-pyrrolidin-1-yl-pteridine: 360 mg (4.2 mmol) piperazine are suspended in 15 ml dioxane and heated to 80° C. A solution of 285 mg (0.84 mmol) 7-cyclobutylamino-2,6-dichloro-4-pyrrolidin-1-yl-pteridine in 15 ml dioxane is slowly added dropwise to this solution. The mixture is stirred for about another 16 h at 80° C. and then the solvent is eliminated from the reaction mixture in vacuo. The residue is purified by chromatography, the solid obtained is triturated with diisopropylether, suction filtered and dried. Yield 192 mg (59% of theoretical).

Example 3

6-chloro-7-((R)-2-hydroxypropyl)amino-)-2-piperazin-1-yl-4-pyrrolidin-1-yl-pteridine (Example compound 24 from Table 1, prepared according to Scheme 1)

a) 2,6-dichloro-7-((R)-2-hydroxypropyl)amino-4-pyrrolidin-1-yl-pteridine: 300 mg (0.99 mmol) 4-pyrrolidin-1-yl-2,6,7-trichloro-pteridine are suspended in 15 ml dioxane and combined with 121 mg (1.6 mmol) (R)-1-amino-propan-2-ol and 185 μl (1.4 mmol) diisopropylethylamine. The mixture is stirred for approx. 16 h at 40° C., combined with 20 ml of water and extracted twice with 20 ml dichloromethane. The organic phase is dried on sodium sulphate and the solvent is eliminated in vacuo. The residue is used in the next step without further purification.

b) 6-chloro-7-((R)-2-hydroxypropyl)amino-2-piperazin-1-yl-4-pyrrolidin-1-yl-pteridine: 440 mg (5.1 mmol) piperazine are suspended in 15 ml dioxane and heated to 80° C. a solution of 349 mg (1 mmol) 2,6-dichloro-7-((R)-2-hydroxypropyl)amino-4-pyrrolidin-1-yl-pteridine in 15 ml dioxane is slowly added dropwise to this solution. The mixture is stirred for roughly another 16 h at 80° C. and then the reaction mixture is freed from the solvent in vacuo. The residue is purified by chromatography, crystallised with ethyl acetate and petroleum ether, suction filtered and dried. Yield 194 mg (49% of theoretical).

Example 4

7-(1,1-bis-(hydroxymethyl)propyl)amino-6-chloro-2-piperazin-1-yl-4-pyrrolidin-1-yl-pteridine (Example compound 33 from Table 1, prepared according to Scheme 1)

a) 7-(1,1-bis-(hydroxymethyl)propyl)amino-2,6-dichloro-4-pyrrolidin-1-yl-pteridine: 65 mg (1 mmol) 1,1-bis-(hydroxymethyl)-propyl)-amine are dissolved in 4 ml of tetrahydrofuran and at −10° C. combined with 0.27 ml (0.55 mmol) of a 2 molar solution of lithium diisopropylamide in tetrahydrofuran. The mixture is stirred for one hour at ambient temperature and cooled to −10° C. again. Then a suspension of 167 mg (0.55 mmol) 4-pyrrolidin-1-yl-2,6,7-trichloro-pteridine in 15 ml dioxane is added dropwise. The mixture is allowed to come up to ambient temperature and stirred for about another 16 h. The reaction mixture is mixed with water and extracted with dichloromethane. The organic phase is dried on sodium sulphate and the solvent is eliminated in vacuo. The residue is purified by chromatography, triturated with ether and suction filtered. Yield 66 mg (31% of theoretical)

b) 7-(1,1-bis-(hydroxymethyl)propyl)amino-6-chloro-2-piperazin-1-yl-4-pyrrolidin-1-yl-pteridine: 1.02 g (12 mmol) piperazine are suspended in 45 ml dioxane and heated to 80° C. A solution of 920 mg (2.4 mmol) 7-(1,1-bis-(hydroxymethyl)propyl)amino-2,6-dichloro-4-pyrrolidin-1-yl-pteridine in 100 ml dioxane is slowly added dropwise to this solution. The mixture is stirred for approx. 16 h at 80° C. and then the reaction mixture is poured onto 30 ml ice water. The mixture is extracted with dichloromethane, the organic phase is dried on sodium sulphate and the solvent is eliminated in vacuo. The residue is taken up in some dichloromethane and combined with ether, the precipitate formed is suction filtered. Yield 1.032 g (99% of theoretical).

Example 5

6-chloro-7-(4,5-dimethylthiazol-2-yl)-amino-2-piperazin-1-yl-4-pyrrolidin-1-yl-pteridine (Example compound 91 from Table 1, prepared according to Scheme 1)

a+b) 100 mg (0.33 mmol) 4-pyrrolidin-1-yl-2,6,7-trichloro-pteridine are dissolved in 5 ml dioxane and combined with 46 mg (0.36 mmol) 2-amino-4,5-dimethyl-thiazole and 50 mg (0.36 mmol) potassium carbonate. The mixture is stirred for 3 hours at 40° C., the precipitate formed is suction filtered and taken up in dioxane. This solution is slowly added dropwise to a solution of 141 mg (2 mmol) piperazine in 15 ml dioxane heated to 80° C. The mixture is stirred for approx. 16 h at 80° C., left to cool and the reaction mixture is poured onto approx. 30 ml ice water. It is extracted with dichloromethane, the organic phase is dried on sodium sulphate and the solvent is eliminated in vacuo. The residue is purified by chromatography. Yield 17 mg (11% of theoretical).

Example 6

6-chloro-7-(5-methylthiazol-2-yl)-amino-2-piperazin-1-yl-4-pyrrolidin-1-yl-pteridine (Example compound 92 from Table 1, prepared according to Scheme 1)

a+b) 100 mg (0.33 mmol) 4-pyrrolidin-1-yl-2,6,7-trichloro-pteridine are dissolved in 5 ml dioxane and combined with 41 mg (0.36 mmol) 2-amino-5-methylthiazole and 41 mg (0.36 mmol) potassium-tert.-butoxide. The mixture is stirred for 3 h at 40° C., allowed to cool and then the reaction mixture is slowly added dropwise to a solution of 141 mg (2 mmol) piperazine in 15 ml dioxane heated to 80° C. The mixture is stirred for approx. 16 h at 80° C., cooled and the solvent is eliminated in vacuo. The residue is purified by chromatography. Yield 5.5 mg (3% of theoretical).

Example 7

6-chloro-7-(4-methylthiazol-2-yl)-amino-2-piperazin-1-yl-4-pyrrolidin-1-yl-pteridine (Example compound 96 according to Table 1, prepared according to Scheme 1)

a) 2,6-dichloro-7-(4-methylthiazol-2-yl)-amino-4-pyrrolidin-1-yl-pteridine: 94 mg (0.82 mmol) 2-amino-4-methylthiazole are dissolved in 15 ml of tetrahydrofuran and at −10° C. combined with 410 µl (0.82 mmol) of a 2 molar solution of lithium diisopropylamide in tetrahydrofuran. The mixture is stirred for one hour at ambient temperature, cooled to −10° C. again and a suspension of 250 mg (0.82 mmol) 4-pyrrolidin-1-yl-2,6,7-trichloro-pteridine in 10 ml of tetrahydrofuran is added dropwise. The mixture is allowed to come up to ambient temperature and stirred for about another 16 h. Water is added and the mixture is extracted with ethyl acetate. The organic phase is dried on sodium sulphate and the solvent is eliminated in vacuo. The residue is triturated with acetonitrile, the precipitate formed is suction filtered and used in the next step without further purification. Yield 105 mg (33% of theoretical).

b) 6-chloro-7-(4-methylthiazol-2-yl)-amino-2-piperazin-1-yl-4-pyrrolidin-1-yl-pteridine: 118 mg (1.37 mmol) piperazine are suspended in 10 ml dioxane and heated to 80° C. A solution of 105 mg (0.28 mmol) 2,6-dichloro-7-(4-methylthiazol-2-yl)-amino-4-pyrrolidin-1-yl-pteridine in 5 ml dioxane is added dropwise and the mixture is stirred for approx. another 16 h at 80° C. The reaction mixture is poured onto ice water and extracted with dichloromethane. The organic phase is dried on sodium sulphate and the solvent is eliminated in vacuo, the residue is triturated with ether and suction filtered. Yield 54 mg (46% of theoretical).

Example 8

6-chloro-7-(3-cyclopropyl-1-hydroxy-prop-2-yl)-amino-2-piperazin-1-yl-4-pyrrolidin-1-yl-pteridine (Example compound 110 from Table 1, prepared according to Scheme 1)

a)+b) 200 mg (0.66 mmol) 4-pyrrolidin-1-yl-2,6,7-trichloro-pteridine are dissolved in 10 ml dioxane and combined with 83.4 mg (0.72 mmol) 2-amino-3-cyclopropyl-propan-1-ol and 121 µl (0.92 mmol) diisopropylethylamine. The mixture is stirred for approx. 16 h at 40° C. The reaction mixture is cooled to ambient temperature, mixed with water and extracted with dichloromethane. The organic phase is dried and the solvent is eliminated in vacuo. The residue is purified by chromatography. 90 mg 7-(3-cyclopropyl-1-hydroxy-prop-2-yl)-amino-2,6-dichloro-4-pyrrolidin-1-yl-pteridine are obtained. 70 mg of this substance are dissolved in 11 ml dioxane. This solution is slowly added dropwise to a solution of 78.9 mg (0.92 mmol) piperazine in 11 ml dioxane at a temperature of 80° C. The mixture is stirred for approx. 16 h at 80° C., cooled to ambient temperature and then poured onto ice water. The mixture is extracted with dichloromethane, the organic phase is dried on sodium sulphate and the solvent is eliminated in vacuo. The residue is purified by chromatography. Yield 79 mg (100% of theoretical).

Example 9

4-azetidin-1-yl-6-chloro-7-cyclobutylamino-2-piperazin-1-yl-pteridine (Example compound 113 from Table 1, prepared according to Scheme 1)

a)+b) 100 mg (0.34 mmol) 4-azetidin-1-yl-2,6,7-trichloro-pteridine are dissolved in 5 ml dioxane and combined with 30 µl (0.35 mmol) cyclobutylamine and 66 µl (0.39 mmol) diisopropylethylamine The mixture is stirred for approx. 16 h at 40° C. The reaction mixture is cooled to ambient temperature and the solvent is eliminated in vacuo. The residue is purified by chromatography (reversed phase). 60 mg (54% of theory) 4-azetidin-1-yl-7-cyclobutylamino-2,6-dichloro-pteridine are obtained. This substance is dissolved in 5 ml dioxane and slowly added dropwise to a solution of 80 mg (0.93 mmol) piperazine in 5 ml dioxane at a temperature of 80° C. The mixture is stirred for approx. one hour at 80° C., cooled to ambient temperature and then mixed with water. The mixture is extracted with dichloromethane, the organic phase is dried on sodium sulphate and the solvent is eliminated in vacuo. Yield 50 mg (72% of theoretical).

Example 10

6-chloro-7-(1-hydroxy-cyclohexylmethyl)-amino-2-piperazin-1-yl-4-pyrrolidin-1-yl-pteridine (Example compound 116 from Table 1, prepared according to Scheme 1)

a)+b) 100 mg (0.33 mmol) 4-pyrrolidin-1-yl-2,6,7-trichloro-pteridine are dissolved in 5 ml dioxane and combined with 60 mg (0.36 mmol) 1-aminomethyl-1-cyclohexanol and 108 µl (0.82 mmol) diisopropylethylamine. The mixture is stirred for approx. 70 h at 40° C. The reaction mixture is then added dropwise to a solution of 141 mg (1.64 mmol) piperazine in 15 ml dioxane at a temperature of 80° C. The mixture is stirred for approx. 16 hours at 80° C., cooled to ambient temperature and then mixed with water. It is extracted with dichloromethane, the organic phase is dried on sodium sulphate and the solvent is eliminated in vacuo. The residue is triturated with diethyl ether, the resulting solid is suction filtered, washed with ether and dried. Yield 100 mg (68% of theoretical).

Example 11

6-chloro-7-(N-methyl-2-hydroxyethyl)-amino-2-piperazin-1-yl-4-pyrrolidin-1-yl-pteridine (Example compound 117 from Table 1, prepared according to Scheme 1)

a)+b) 100 mg (0.33 mmol) 4-pyrrolidin-1-yl-2,6,7-trichloro-pteridine are dissolved in 5 ml dioxane and combined with 27.1 mg (0.36 mmol) 2-methylaminoethanol and 61 µl (0.36 mmol) diisopropylethylamine. The mixture is stirred for approx. 70 h at 40° C. The reaction mixture is cooled to ambient temperature, mixed with water and extracted with dichloromethane. The organic phase is dried and the solvent is eliminated in vacuo. The residue is purified by chromatography. 100 mg 2,6-dichloro-7-(N-methyl-2-hydroxyethyl)-amino-4-pyrrolidin-1-yl-pteridine are obtained, which are dissolved in 5 ml dioxane and slowly added dropwise to a solution of 141 mg (1.64 mmol) piperazine in 15 ml dioxane at a temperature of 80° C. The mixture is stirred for approx. 16 hours at 80° C., cooled to ambient temperature and then mixed with water. It is extracted with dichloromethane, the organic phase is dried on sodium sulphate and the solvent is eliminated in vacuo. The residue is purified by chromatography. Yield 130 mg (still contains solvent).

All the example compounds from Table 1 which are marked "Scheme 1" are prepared analogously to Scheme 1 and analogously to the detailed methods of synthesis described above.

The following example compounds were prepared according to Scheme 2:

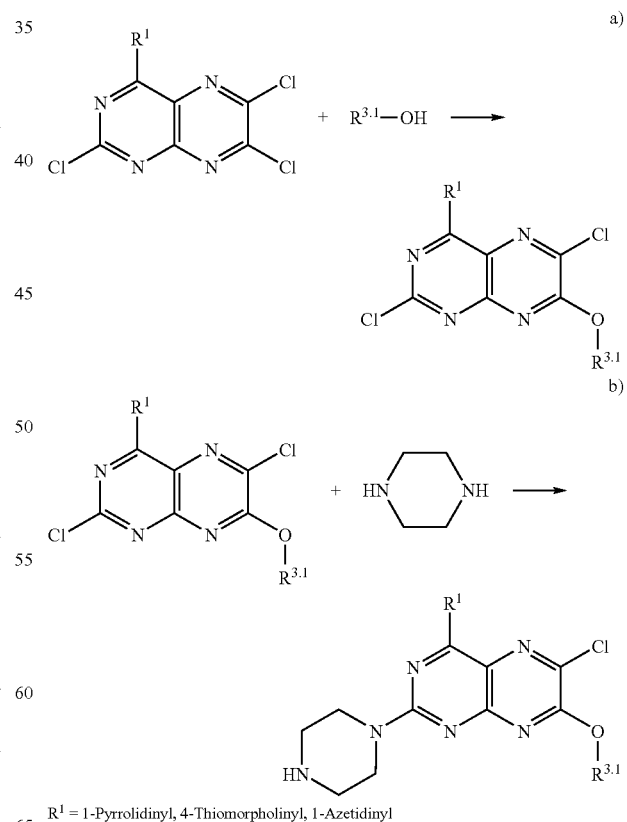

$R^1$ = 1-Pyrrolidinyl, 4-Thiomorpholinyl, 1-Azetidinyl

Example 12

6-chloro-7-cyclopropylmethyloxy-2-piperazin-1-yl-4-pyrrolidin-1-yl-pteridine (Example compound 81 from Table 1, prepared according to Scheme 2)

a) 7-cyclopropylmethyloxy-2,6-dichloro-4-pyrrolidin-1-yl-pteridine: 0.067 ml (0.82 mmol) cyclopropylmethanol are dissolved in 12 ml of tetrahydrofuran and under argon combined with 0.41 ml (0.82 mmol) of a 2 molar solution of lithium diisopropylamide in tetrahydrofuran. The mixture is stirred for 30 min at ambient temperature, then it is slowly added to a solution of 250 mg (0.82 mmol) 4-pyrrolidin-1-yl-2,6,7-trichloro-pteridine in 12 ml of tetrahydrofuran cooled to −10° C. The mixture is stirred for one hour at −10° C., slowly allowed to come up to ambient temperature and combined with 25 ml of water. The reaction mixture is extracted with dichloromethane, the organic phase is dried on sodium sulphate and the solvent is eliminated in vacuo. The residue is purified by chromatography. Yield 141 mg (51% of theoretical)

b) 6-chloro-7-cyclopropylmethyloxy-2-piperazin-1-yl-4-pyrrolidin-1-yl-pteridine: A solution of 158 mg (1.8 mmol) piperazine in 10 ml of tetrahydrofuran is slowly added dropwise at ambient temperature to a solution of 139 mg (0.41 mmol) 7-cyclopropylmethyloxy-2,6-dichloro-4-pyrrolidin-1-yl-pteridine in 15 ml of tetrahydrofuran. Then the mixture is refluxed for approx. 16 h. The reaction mixture is freed from the solvent in vacuo, the residue is purified by chromatography. Yield 120 mg (75% of theoretical)

Example 13

6-chloro-7-((R)-3-tetrahydrofuryl)-oxy-2-piperazin-1-yl-4-thiomorpholin-4-yl-pteridine (Example compound 56 from Table 1, prepared according to Scheme 2)

a)+b) 65 mg (0.74 mmol) (R)-3-hydroxytetrahydrofuran are dissolved in 3 ml of tetrahydrofuran and under protective gas combined at −10° C. with 371 μl (0.74 mmol) of a 2 molar solution of lithium diisopropylamine in tetrahydrofuran. The mixture is slowly allowed to come up to ambient temperature and stirred for another hour. It is cooled to −10° C. again and a suspension of 250 mg (0.74 mmol) 4-thiomorpholin-4-yl-2,6,7-trichloro-pteridine in 9 ml of tetrahydrofuran is slowly added. The mixture is stirred for another 1 hour at −10° C. and then slowly allowed to come up to ambient temperature. The reaction mixture is mixed with water and extracted with dichloromethane. The organic phase is dried on sodium sulphate and the solvent is eliminated in vacuo. The residue is taken up in 10 ml dioxane and slowly added dropwise to a solution of 320 mg (3.7 mmol) piperazine in 5 ml dioxane at a temperature of 80° C. The mixture is stirred for one more hour at 80° C., cooled to ambient temperature and the reaction mixture is combined with water. It is extracted with dichloromethane, the organic phase is dried on sodium sulphate and the solvent is eliminated in vacuo. The residue is purified by chromatography. Yield 142 mg (35% of theoretical)

Example 14

6-chloro-7-(2,2-difluorethyloxy)-2-piperazin-1-yl-4-pyrrolidin-1-yl-pteridine (Example compound 104 from Table 1, prepared according to Scheme 2)

a)+b) 50 μl (0.82 mmol) 2,2-difluorethanol are dissolved in 12 ml of tetrahydrofuran and under protective gas combined with 410 μl (0.82 mmol) of a 2 molar solution of lithium diisopropylamine in tetrahydrofuran. The mixture is stirred for 30 minutes and then the mixture is added to a solution of 250 mg (0.82 mmol) 4-pyrrolidin-1-yl-2,6,7-trichloro-pteridine in 12 ml of tetrahydrofuran cooled to −10° C. The mixture is stirred for one hour at −10° C., slowly allowed to come up to ambient temperature and stirred for another four hours. The solvent is eliminated in vacuo, the residue is combined with 50 ml of water and extracted with dichloromethane. The organic phase is dried on sodium sulphate and the solvent is eliminated in vacuo. The residue is taken up in 15 ml of tetrahydrofuran and combined with a solution of 313 mg (3.6 mmol) piperazine in 10 ml of tetrahydrofuran. The mixture is refluxed for approx. 16 hours, cooled to ambient temperature and the solvent is eliminated in vacuo. The residue is mixed with water and extracted with dichloromethane. The organic phase is dried on sodium sulphate and the solvent is eliminated in vacuo. Diisopropylether is added and a yellowish solid is obtained. Yield 225 mg (70% of theoretical)

Example 15

6-chloro-7-hydroxy-2-piperazin-1-yl-4-pyrrolidin-1-yl-pteridine (Example compound 105 from Table 1, prepared according to Scheme 2)

a)+b) 460 μl (0.82 mmol) of a 10% solution of potassium hydroxide in water is added dropwise to a solution of 250 mg (0.82 mmol) 4-pyrrolidin-1-yl-2,6,7-trichloro-pteridine in 15 ml of tetrahydrofuran cooled to −10° C. The mixture is stirred for one hour at −10° C., slowly allowed to come up to ambient temperature and stirred for approx. another 16 hours. Then a solution of 318 mg (3.69 mmol) piperazine in 10 ml of tetrahydrofuran is added and the mixture is refluxed for approx. 16 hours. Then the solvent is eliminated in vacuo, the residue is mixed with water and extracted with dichloromethane. The organic phase is dried on sodium sulphate and the solvent is eliminated in vacuo. The residue is purified by chromatography. Yield 50 mg (14% of theoretical)

Example 16

(R)-6-chloro-7-(3-tetrahydropyranyloxy)-2-piperazin-1-yl-4-pyrrolidin-1-yl-pteridine (Example compound 112 from Table 1, prepared according to Scheme 2)

a)+b) 170 mg (1.67 mmol) (R)-3-hydroxytetrahydropyran are dissolved in 5 ml of tetrahydrofuran and under protective gas at −10° C. mixed with 821 μl (1.64 mmol) of a 2 molar solution of lithium diisopropylamine in tetrahydrofuran. The mixture is stirred for 30 minutes at −10° C., then for one hour at ambient temperature. The mixture is cooled to −10° C. again and combined with a suspension of 500 mg (1.64 mmol) 4-pyrrolidin-1-yl-2,6,7-trichloropteridine in 15 ml of tetrahydrofuran. The mixture is stirred for one hour at −10° C., slowly allowed to come up to ambient temperature and stirred for another four hours. The reaction mixture is combined with approx. 100 ml of water and extracted with dichloromethane. The organic phase is dried on sodium sulphate and the solvent is eliminated in vacuo. The residue is taken up in approx. 50 ml diethyl ether and stirred for one hour. The solid is suction filtered, washed with diethyl ether and dried. Yield 320 mg (53% of theory). The (R)-2,6-dichloro-7-(3-tetrahydropyranyloxy)-4-pyrrolidin-1-yl-pteridine thus obtained is dissolved in 13 ml dioxane and slowly added dropwise to a solution of 372 mg (4.3 mmol) piperazine in 12 ml dioxane at a temperature of 80° C. The mixture is stirred for approx. another 16 hours at 80° C., cooled to ambient temperature and the reaction mixture is combined with water. It is extracted with dichloromethane, the organic phase is dried on sodium sulphate and the solvent is eliminated in vacuo. The residue is purified by chromatography. The product obtained is stirred with diethyl ether, the solid substance is suction filtered, washed with diethyl ether and dried. Yield 170 mg (47% of theoretical)

Example 17

4-azetidin-1-yl-6-chloro-7-(tetrahydropyran-4-yloxy)-2-piperazin-1-yl-pteridine (Example compound 114 from Table 1, prepared according to Scheme 2)

a)+b) 56 µl (0.59 mmol) 4-hydroxytetrahydropyran are dissolved in 2 ml of tetrahydrofuran and under protective gas at −10° C. mixed with 293 µl (0.59 mmol) of a 2 molar solution of lithium diisopropylamine in tetrahydrofuran. The mixture is stirred for 30 minutes at −10° C., then for one hour at ambient temperature. The mixture is cooled to −10° C. again and combined with a suspension of 170 mg (0.59 mmol) 4-azetidin-1-yl-2,6,7-trichloro-pteridine in 5 ml of tetrahydrofuran. The mixture is stirred for one hour at −10° C., slowly allowed to come up to ambient temperature and stirred for approx. another 16 hours. The reaction mixture is mixed with water and extracted with dichloromethane. The organic phase is dried on sodium sulphate and the solvent is eliminated in vacuo. The residue is purified by chromatography (reversed phase). 90 mg of 4-azetidin-1-yl-2,6-dichloro-7-(tetrahydropyran-4-yloxy)-pteridine are obtained, which is dissolved in 5 ml dioxane and slowly added dropwise to a solution of 109 mg (1.27 mmol) piperazine in 5 ml dioxane at a temperature of 80° C. The mixture is stirred for approx. another 1 hour at 80° C., cooled to ambient temperature and the reaction mixture is combined with water. It is extracted with dichloromethane, the organic phase is dried on sodium sulphate and the solvent is eliminated in vacuo. Yield 70 mg (68% of theoretical)

Example 18

(R)-4-azetidin-1-yl-6-chloro-7-(tetrahydrofuran-3-yl-oxy)-2-piperazin-1-yl-pteridine (Example compound 115 from Table 1, prepared according to Scheme 2)

a)+b) 111 µl (1.38 mmol) (R)-3-hydroxytetrahydrofuran are dissolved in 5 ml of tetrahydrofuran and under protective gas at −10° C. mixed with 688 µl (1.38 mmol) of a 2 molar solution of lithium diisopropylamine in tetrahydrofuran. The mixture is stirred for 30 minutes at −10° C., then for one hour at ambient temperature. The mixture is cooled to −10° C. again and combined with a suspension of 400 mg (1.38 mmol) 4-azetidin-1-yl-2,6,7-trichloro-pteridine in 10 ml of tetrahydrofuran. The mixture is stirred for one hour at −10° C., slowly allowed to come up to ambient temperature and stirred for approx. another 16 hours. The reaction mixture is mixed with water and extracted with dichloromethane. The organic phase is dried on sodium sulphate and the solvent is eliminated in vacuo. The residue is stirred with diethyl ether, the precipitated solid is suction filtered, washed with diethyl ether and dried. 290 mg (R)-4-azetidin-1-yl-2,6-dichloro-7-(tetrahydrofuran-3-yl-oxy)-pteridine is obtained, which is dissolved in 13 ml dioxane and slowly added dropwise to a solution of 365 mg (4.24 mmol) piperazine in 12 ml dioxane at a temperature of 80° C. The mixture is stirred for approx. another 16 hours at 80° C., cooled to ambient temperature and water is added to the reaction mixture. It is extracted with dichloromethane, the organic phase is dried on sodium sulphate and purified by chromatography. Yield 170 mg (51% of theoretical)

All the example compounds from Table 1 which are marked "Scheme 2" are prepared analogously to Scheme 2 and analogously to the detailed methods of synthesis described above.

The following example compounds were prepared according to Scheme 3:

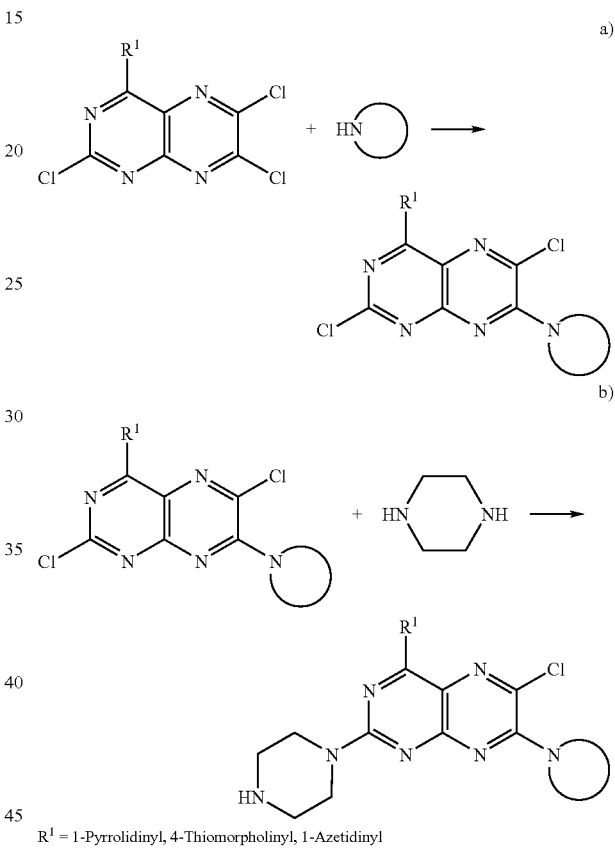

Example 19

6-chloro-7-(4-hydroxypiperidin-1-yl)-2-piperazin-1-yl-4-pyrrolidin-1-yl-pteridine (Example compound 64 from Table 1, prepared according to Scheme 3)

a)+b) 80 mg (0.26 mmol) 4-pyrrolidin-1-yl-2,6,7-trichloro-pteridine are dissolved in 5 ml dioxane and combined with 29 mg (0.29 mmol) 4-hydroxypiperidin and 49 µl (0.37 mmol) diisopropylethylamine. The mixture is stirred for approx. 16 h at 40° C. The reaction mixture is then slowly added dropwise to a solution of 113 mg (1 mmol) piperazine in 15 ml dioxane at a temperature of 80° C. The mixture is stirred for approx. 16 h at 80° C., cooled to ambient temperature and then poured onto ice water. It is extracted with dichloromethane, the organic phase is dried on sodium sulphate and the solvent is eliminated in vacuo. The residue is taken up in some dichloromethane and combined with petroleum ether, the precipitate formed is suction filtered. Yield 58 mg (53% of theoretical).

Example 20

6-chloro-7-((R)-3-hydroxypyrrolidin-1-yl)-2-piperazin-1-yl-4-pyrrolidin-1-yl-pteridine (Example compound 49 from Table 1, prepared according to Scheme 3)

a)+b) 80 mg (0.26 mmol) 4-pyrrolidin-1-yl-2,6,7-trichloro-pteridine are dissolved in 5 ml dioxane and combined with 72 mg (0.58 mmol) (R)-3-hydroxypyrrolidin and 100 µl (0.75 mmol) diisopropylethylamine The mixture is stirred for approx. 30 h at 40° C. The reaction mixture is then slowly added dropwise to a solution of 113 mg (1 mmol) piperazine in 15 ml dioxane at a temperature of 80° C. The mixture is stirred for approx. 16 h at 80° C., cooled to ambient temperature and then poured onto ice water. It is extracted with dichloromethane, the organic phase is dried on sodium sulphate and the solvent is eliminated in vacuo. The residue is purified by chromatography. Yield 68.8 mg (65% of theoretical).

Example 21

6-chloro-7-(3,4-dihydro-2H-1-benzopyran-4-yl)-oxy-2-piperazin-1-yl-4-pyrrolidin-1-yl-pteridine (Example compound 88 from Table 1, prepared according to Scheme 2)

a) 2,6-dichloro-7-(3,4-dihydro-2H-1-benzopyran-4-yl)-oxy-4-pyrrolidin-1-yl-pteridine: 100 mg (0.66 mmol) 4-chromanol are dissolved in 5 ml of tetrahydrofuran and at −10° C. under argon mixed with 330 µl (0.66 mmol) of a 2 molar solution of lithium diisopropylamide in tetrahydrofuran. The mixture is stirred for 30 min at ambient temperature, then cooled to −10° C. and a solution of 200 mg (0.66 mmol) 4-pyrrolidin-1-yl-2,6,7-trichloro-pteridine in 10 ml of tetrahydrofuran is slowly added dropwise to the mixture. The resulting mixture is stirred for one hour at −10° C. and left overnight to come up to ambient temperature. Water is added and the reaction mixture is extracted with dichloromethane. The organic phase is dried on sodium sulphate and the solvent is eliminated in vacuo. The residue is purified by chromatography. Yield 138 mg (50% of theoretical)

b) 6-chloro-7-(3,4-dihydro-2H-1-benzopyran-4-yl)-oxy-2-piperazin-1-yl-4-pyrrolidin-1-yl-pteridine:
A solution of 136 mg (0.33 mmol) 2,6-dichloro-7-(3,4-dihydro-2H-1-benzopyran-4-yl)-oxy-4-pyrrolidin-1-yl-pteridine in 4 ml dioxane is added dropwise to a solution of 60 mg (0.7 mmol) piperazine in 1 ml dioxane at a temperature of 80° C. and stirred for approx. 16 h at 80° C. The reaction mixture is freed from the solvent in vacuo, the residue is purified by chromatography. Yield 141 mg (93% of theoretical).

Example 22

6-chloro-2-piperazin-1-yl-4-pyrrolidin-1-yl-7-thiazolidin-3-yl-pteridine (Example compound 100 from Table 1, prepared according to Scheme 3)

a)+b) 250 mg (0.82 mmol) 4-pyrrolidin-1-yl-2,6,7-trichloro-pteridine are dissolved in 10 ml dioxane and combined with 73 µl (1 mmol) thiazolidine and 200 µl (1.1 mmol) diisopropylethylamine. The mixture is stirred for approx. 16 h at 40° C. The reaction mixture is then slowly added dropwise to a solution of 354 mg (4 mmol) piperazine in 15 ml dioxane at a temperature of 80° C. The mixture is stirred for approx. 16 h at 80° C., cooled to ambient temperature and then poured onto ice water. It is extracted with dichloromethane, the organic phase is dried on sodium sulphate and the solvent is eliminated in vacuo. The residue is purified by chromatography. Yield 334 mg (54% of theoretical).

Example 23

6-chloro-7-(4-phenylpiperazin-1-yl)-2-piperazin-1-yl-4-pyrrolidin-1-yl-pteridine (Example compound 102 from Table 1, prepared according to Scheme 3)

a)+b) 250 mg (0.82 mmol) 4-pyrrolidin-1-yl-2,6,7-trichloro-pteridine are dissolved in 10 ml dioxane and combined with 138 µl (1 mmol) 1-phenylpiperazine and 200 µl (1.1 mmol) diisopropylethylamine. The mixture is stirred for approx. 16 h at 40° C. The reaction mixture is then slowly added dropwise to a solution of 354 mg (4 mmol) piperazine in 15 ml dioxane at a temperature of 80° C. The mixture is stirred for approx. 5 h at 80° C., cooled to ambient temperature and then poured onto ice water. It is extracted with dichloromethane, the organic phase is dried on sodium sulphate and the solvent is eliminated in vacuo. The residue is purified by chromatography. Yield 332 mg (84% of theoretical).

Example 24

6-chloro-7-(3-(4-morpholinyl-methyl)-piperidin-1-yl)-2-piperazin-1-yl-4-pyrrolidin-1-yl-pteridine (Example compound 106 from Table 1, prepared according to Scheme 3)

a)+b) 100 mg (0.33 mmol) 4-pyrrolidin-1-yl-2,6,7-trichloro-pteridine are dissolved in 7 ml dioxane and combined with 61 mg (0.33 mmol) 3-(4-morpholinyl-methyl)-piperidine and 65 µl (0.49 mmol) diisopropylethylamine The mixture is stirred for approx. 16 h at 40° C. The reaction mixture is then slowly added dropwise to a solution of 141 mg (1.6 mmol) piperazine in 15 ml dioxane at a temperature of 80° C. It is stirred for approx. 16 h at 80° C., cooled to ambient temperature and then poured onto ice water. It is extracted with dichloromethane, the organic phase is dried on sodium sulphate and the solvent is eliminated in vacuo. The residue is taken up in some dichloromethane and mixed with petroleum ether, the precipitate formed is suction filtered. Yield 80 mg (49% of theoretical).

Example 25

(S)-6-chloro-7-(2-methyl-piperidin-1-yl)-2-piperazin-1-yl-4-pyrrolidin-1-yl-pteridine (Example compound 107 from Table 1, prepared according to Scheme 3)

a)+b) 300 mg (0.99 mmol) 4-pyrrolidin-1-yl-2,6,7-trichloro-pteridine are dissolved in 15 ml dioxane and combined with 131 µl (1.08 mmol) (S)-(+)-2-methylpiperidine and 182 µl (1.38 mmol) diisopropylethylamine. The mixture is stirred for approx. 70 h at 40° C. The reaction mixture is cooled to ambient temperature, mixed with water and extracted with dichloromethane. The organic phase is dried and the solvent is eliminated in vacuo. 367 mg of a yellow solid are obtained. 345 mg of this solid are dissolved in 15 ml dioxane and slowly added dropwise to a solution of 405 mg (4.7 mmol) piperazine in 15 ml dioxane at a temperature of 80° C. The mixture is stirred for approx. 16 h at 80° C., cooled to ambient temperature and then poured onto ice water. It is extracted with dichloromethane, the organic phase is dried on sodium sulphate and the solvent is eliminated in vacuo. The residue is mixed with ether, the precipitate formed is suction filtered. Yield 280 mg (71% of theoretical).

Example 26

(R)-6-chloro-7-(2-methyl-piperidin-1-yl)-2-piperazin-1-yl-4-pyrrolidin-1-yl-pteridine (Example compound 108 from Table 1, prepared according to Scheme 3)

a)+b) 1.5 g (4.93 mmol) 4-pyrrolidin-1-yl-2,6,7-trichloro-pteridine are dissolved in 50 ml dioxane and combined with 653 µl (5 mmol) (R)-(+)-2-methylpiperidine and 910 µl (6.9 mmol) diisopropylethylamine. The mixture is stirred for approx. 70 h at 40° C. The reaction mixture is cooled to ambient temperature, mixed with water and extracted with dichloromethane. The organic phase is dried and the solvent is eliminated in vacuo. The residue is combined with 40 ml ether and stirred for 15 minutes. The precipitate is suction filtered, washed with ether and dried. 1.4 g of a solid is obtained, which is dissolved in 60 ml dioxane. This solution is slowly added dropwise to a solution of 1.642 g (19 mmol) piperazine in 60 ml dioxane at a temperature of 80° C. The mixture is stirred for approx. 16 h at 80° C., cooled to ambient temperature and then poured onto ice water. It is extracted with dichloromethane, the organic phase is dried on sodium sulphate and the solvent is eliminated in vacuo. The residue is purified by chromatography. Yield 1.22 g (77% of theoretical).

Example 27

6-chloro-7-(3-hydroxymethyl-morpholin-4-yl)-2-piperazin-1-yl-4-pyrrolidin-1-yl-pteridine (Example compound III from Table 1, prepared according to Scheme 3)

a)+b) 200 mg (0.66 mmol) 4-pyrrolidin-1-yl-2,6,7-trichloro-pteridine are dissolved in 10 ml dioxane and mixed with 84.8 mg (0.72 mmol) 3-hydroxymethylmorpholine and 121 µl (0.92 mmol) diisopropylethylamine. The mixture is stirred for approx. 16 h at 40° C. The reaction mixture is cooled to ambient temperature, mixed with water and extracted with dichloromethane. The organic phase is dried and the solvent is eliminated in vacuo. The residue is purified by chromatography. 60 mg of the 7-(3-hydroxymethyl-morpholin-4-yl)-2,6-dichloro-4-pyrrolidin-1-yl-pteridine thus obtained are dissolved in 10 ml dioxane and slowly added dropwise to a solution of 67.3 mg (0.78 mmol) piperazine in 10 ml dioxane at a temperature of 80° C. The mixture is stirred for approx. 16 h at 80° C., cooled to ambient temperature and then poured onto ice water. It is extracted with dichloromethane, the organic phase is dried on sodium sulphate and the solvent is eliminated in vacuo. The residue is purified by chromatography. Yield 40 mg (59% of theoretical).

All the example compounds from Table 1 marked "Scheme 3" are prepared analogously to Scheme 3 and analogously to the detailed methods of synthesis described above.

The following non-commercial components $NR^{3.1}R^{3.2}$, $OR^{3.1}$ or

of reaction schemes 1, 2 or 3 were synthesised as follows:

The preparation of the (S)-2-(pyrrolidin-2-yl)propan-2-ol used for Example 3 is described in: Enders, Dieter; Kiphardt, Helmut; Gerdes, Peter; Brena-Valle, Leonardo J.; Bhushan, Vidya., Bulletin des Societes Chimiques Belges (1988), 97(8-9), 691-704. The (R)-2-(pyrrolidin-2-yl)propan-2-ol used for Example 4 is prepared analogously.

The preparation of the 4-amino-1-tetrahydro-4H-pyran-4-yl-piperidine used for Example 90 in the Table is described in: Hoffmann, Matthias; Grauert, Matthias; Brandl, Trixi; Breitfelder, Steffen; Eickmeier, Christian; Steegmaier, Martin; Schnapp, Gisela; Baum, Anke; Quant, Jens Juergen; Solca, Flavio; Colbatzky, Florian. U.S. Pat. Appl. Publ. (2004), 109 pp., US 2004176380 A1.

The preparation of the 1-amino-1-hydroxymethyl-cyclohexane used for Example 36 of the Table is described in: Meinzer, Alexandra; Breckel, Andrea; Thaher, Bassam Abu; Manicone, Nico; Otto, Hans-Hartwig. Helvetica Chimica Acta (2004), 87(1), 90-105.

The preparation of the (3R,4R)-pyrrolidine-3,4-diol used for Example 5 of the Table and of the (3S,4S)-pyrrolidine-3,4-diol used for Example 6 is described in: Lysek, Robert; Vogel, Pierre. Helvetica Chimica Acta (2004), 87(12), 3167-3181.

The 3-phenyl-cyclopentylamine used for Example 77 of the Table is prepared as described below:

a) 3-phenylcyclopentanone-oxime: 2.07 g ((29.8 mmol) hydroxylamine are dissolved in 4 ml of water and 7 ml of methanol. To this is added dropwise a solution of 2.2 g (13.7 mmol) 3-phenylpentanone in 50 ml of methanol. 1.89 g (13.7 mmol) potassium carbonate and 9 ml of water are added and the mixture is stirred for 2.5 h at ambient temperature. The reaction mixture is freed from the solvent in vacuo, the residue is taken up in 130 ml of ethyl acetate. The organic phase is washed twice with 50 ml of water, the aqueous phases are counter-washed with 50 ml of ethyl acetate. The combined organic phases are dried on sodium sulphate and the solvent is eliminated in vacuo. Yield 2.26 g (94% of theoretical).

b) 3-phenyl-cyclopentylamine: 2.2 g (12.6 mmol) 3-phenyl-cyclopentanone-oxime in 23 ml of methanol are combined with 4 ml of 24% ammonia solution and 2.2 g Raney nickel and hydrogenated at ambient temperature at 60 psi hydrogen pressure until the hydrogen uptake has ended. Then another 1 g catalyst is added and again the mixture is hydrogenated until the hydrogen uptake has ended. The catalyst is filtered off and the solvent is eliminated in vacuo. Yield 1.73 g (86% of theoretical).

The synthesis of 4-pyrrolidinyl-2,6,7-trichloropteridine, which serves as the starting product for synthesis schemes 1, 2 and 3, is described in Merz, K.-H.; Marko, D.; Regiert, T.; Reiss, G.; Frank, W.; Eisenbrand, G. J. Med. Chem. (1998), 41, 4733-4743

The synthesis of tetrachloropteridine, which serves as a starting product for the synthesis of e.g. 4-pyrrolidinyl-2,6,7-trichloropteridine, is described in: Schöpf, C.; Reichert, R.; Riefstahl, K. Liebigs Ann. Chem. (1941), 548, 82-94.

The 4-thiomorphorlin-4-yl-2,6,7-trichloropteridine used for Examples 54-56 of the Table is prepared as follows:

10 g (37 mmol) tetrachloropteridine are dissolved in 190 ml chloroform and combined with a solution of 6.22 g (74 mmol) sodium hydrogen carbonate in 70 ml of water. The mixture is stirred and cooled in the ice bath. A solution of 3.73 ml (37 mmol) thiomorpholine in 20 ml chloroform is slowly added dropwise. The mixture is stirred for another hour while cooling with ice, then it is heated to ambient temperature and the organic phase is separated off. Any precipitate formed is left in the aqueous phase. The aqueous phase is diluted further with water and extracted with chloroform. The combined organic phases are washed with a little water, dried on sodium sulphate and the solvent is eliminated in vacuo. The residue is recrystallised twice from ethyl acetate. Yield 5.5 g (44% of theoretical).

The (S)-2-amino-2-cyclopropylethanol required for Example 109 in the Table is prepared as follows:

500 mg (4.3 mmol) L-cyclopropylglycine are dissolved in 5 ml of tetrahydrofuran. The solution is cooled to 0° C. and 8.69 ml (8.69 mmol) of a 1 molar solution of lithium aluminium hydride in tetrahydrofuran is cautiously added so that the temperature of the reaction mixture does not exceed 10° C. The resulting suspension is stirred for approx. 16 hours at ambient temperature. Then a little water is cautiously added, Celite® 545 is added and the mixture is suction filtered through Celite® 545. It is washed with tetrahydrofuran, the filtrate is freed from the solvent in vacuo. The residue is used without further purification for the next stage of the synthesis.

The synthesis of the (R)-3-hydroxytetrahydropyran used for Example 112 of the Table is described in Brown, H. C. and Vara Prasad, J. V. N.; J. Am. Chem. Soc. (1986), 108, 2049-2054.

The 4-azetidin-1-yl-2,6,7-trichloropteridine needed for Examples 113, 114 and 115 of the Table is prepared as follows:

2 g (7.4 mmol) tetrachloropteridine are dissolved in approx. 150 ml chloroform and combined with a solution of 1.25 g (14 mmol) sodium hydrogen carbonate in 60 ml of water. The mixture is cooled to 0° C., combined with a solution of 0.5 ml (7.4 mmol) azetidine in approx. 50 ml chloroform and stirred for another hour at 0° C. Then the organic phase is separated off, washed with water, dried on sodium sulphate and the solvent is eliminated in vacuo. The residue is triturated with ether and suction filtered. Yield 780 mg (36% of theoretical), the substance is used without further purification for the next stages.

Table 1 that follows is a compilation, by way of example, of compounds which can be prepared using one of the methods of synthesis described hereinbefore. Either the melting point $(m_p)$ is given in ° C. or the respective M+H– value is given for the mass-spectroscopic characterisation of the compound in question.

These compounds are suitable as PDE4 inhibitors and have $IC_{50}$ values of less than or equal to 1 μmol.

To illustrate the present invention further, compounds of formula 1 were prepared,

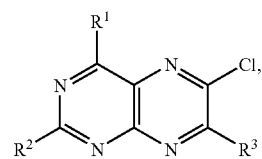

wherein $R^1$, $R^2$ and $R^3$ are defined as follows.

TABLE 1

| # | $R^1$ | $R^2$ | $R^3$ | method of preparation | M + H or $m_p$ |
|---|---|---|---|---|---|
| 1 | *—N(pyrrolidine) | *—N(piperazine)NH | (hydroxy-aminoindane) | Scheme 1 | 467/469 |
| 2 | *—N(pyrrolidine) | *—N(piperazine)NH | (hydroxy-aminoindane, other stereo) | Scheme 1 | 467/469 |
| 3 | *—N(pyrrolidine) | *—N(piperazine)NH | (2-(1-hydroxy-1-methylethyl)pyrrolidinyl) | Scheme 3 | 447/449 |

TABLE 1-continued

| # | R¹ | R² | R³ | method of preparation | M + H or m$_p$ |
|---|---|---|---|---|---|
| 4 | pyrrolidin-1-yl | piperazin-1-yl | 2-(1-hydroxy-1-methylethyl)pyrrolidin-1-yl | Scheme 3 | 447/449 |
| 5 | pyrrolidin-1-yl | piperazin-1-yl | (3,4-dihydroxy)pyrrolidin-1-yl (trans) | Scheme 3 | 421/423 |
| 6 | pyrrolidin-1-yl | piperazin-1-yl | (3,4-dihydroxy)pyrrolidin-1-yl (cis) | Scheme 3 | 421/423 |
| 7 | pyrrolidin-1-yl | piperazin-1-yl | 2-(hydroxymethyl)pyrrolidin-1-yl | Scheme 3 | 407/409 |
| 8 | pyrrolidin-1-yl | piperazin-1-yl | 2-(methoxymethyl)pyrrolidin-1-yl | Scheme 3 | 433/435 |
| 9 | pyrrolidin-1-yl | piperazin-1-yl | morpholin-4-yl | Scheme 3 | 405/407 |
| 10 | pyrrolidin-1-yl | piperazin-1-yl | (1-(hydroxymethyl)cyclopentyl)amino | Scheme 1 | 485/487 |
| 11 | pyrrolidin-1-yl | piperazin-1-yl | (2-hydroxyethyl)amino | Scheme 1 | 378/381 |
| 12 | pyrrolidin-1-yl | piperazin-1-yl | (1,3-dihydroxyprop-2-yl)amino | Scheme 1 | 409/411 |
| 13 | pyrrolidin-1-yl | piperazin-1-yl | (2,3-dihydroxypropyl)amino | Scheme 1 | 409/411 |
| 14 | pyrrolidin-1-yl | piperazin-1-yl | (1,3-dihydroxy-2-methylprop-2-yl)amino | Scheme 1 | 423/425 |

TABLE 1-continued
| # | R¹ | R² | R³ | method of preparation | M + H or $m_p$ |
|---|---|---|---|---|---|
| 15 | 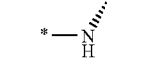 | 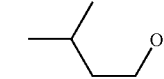 | 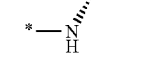 | Scheme 1 | 433/435 |
| 16 | 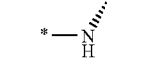 | 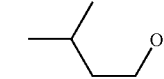 | 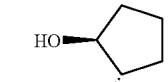 | Scheme 1 | 421/423 |
| 17 | 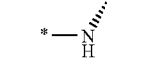 | 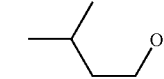 | 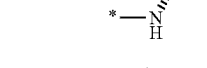 | Scheme 1 | 419/421 |
| 18 | 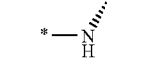 | 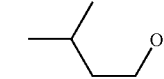 | 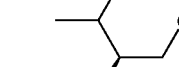 | Scheme 1 | 421/423 |
| 19 | 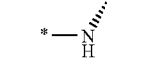 | 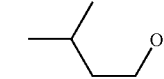 | 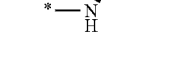 | Scheme 1 | 509/511 |
| 20 | 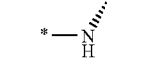 | 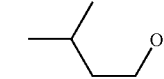 | 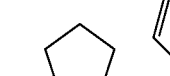 | Scheme 3 | 481/483 |
| 21 | 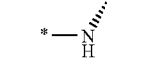 | 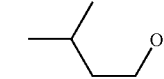 |  | Scheme 1 | 423/425 |
| 22 | 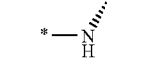 | 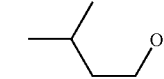 | 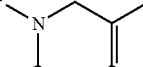 | Scheme 1 | 407/409 |
| 23 | 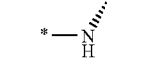 | 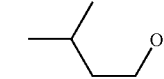 | | Scheme 1 | 393/395 |
| 24 | 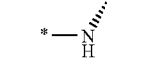 | 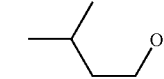 | | Scheme 1 | 393/395 |

TABLE 1-continued

| # | R¹ | R² | R³ | method of preparation | M + H or $m_p$ |
|---|---|---|---|---|---|
| 25 | *—N⟨pyrrolidine⟩ | *—N⟨piperazine⟩NH | (2R)-1-(NH*)-propan-2-ol | Scheme 1 | 393/395 |
| 26 | *—N⟨pyrrolidine⟩ | *—N⟨piperazine⟩NH | (2S)-2-(NH*)-4-methylpentan-1-ol | Scheme 1 | 435/437 |
| 27 | *—N⟨pyrrolidine⟩ | *—N⟨piperazine⟩NH | (2R)-2-(NH*)-4-methylpentan-1-ol | Scheme 1 | 435/437 |
| 28 | *—N⟨pyrrolidine⟩ | *—N⟨piperazine⟩NH | 2-(NH*)-butan-1-ol | Scheme 1 | 407/409 |
| 29 | *—N⟨pyrrolidine⟩ | *—N⟨piperazine⟩NH | (2S)-2-(NH*)-propan-1-ol | Scheme 1 | 393/395 |
| 30 | *—N⟨pyrrolidine⟩ | *—N⟨piperazine⟩NH | 1-(NH*)-2-methyl-propan-2-ol | Scheme 1 | 407/409 |
| 31 | *—N⟨pyrrolidine⟩ | *—N⟨piperazine⟩NH | (2S,3S)-2-(NH*)-3-methylpentan-1-ol | Scheme 1 | 435/437 |
| 32 | *—N⟨pyrrolidine⟩ | *—N⟨piperazine⟩NH | 3-hydroxybutan-2-yloxy* | Scheme 2 | 408/410 |
| 33 | *—N⟨pyrrolidine⟩ | *—N⟨piperazine⟩NH | 2-(NH*)-2-(hydroxymethyl)butan-1-ol | Scheme 1 | 437/439 |
| 34 | *—N⟨pyrrolidine⟩ | *—N⟨piperazine⟩NH | (3R,4S)-4-hydroxytetrahydrofuran-3-yloxy* | Scheme 2 | 422/424 |
| 35 | *—N⟨pyrrolidine⟩ | *—N⟨piperazine⟩NH | 2-hydroxyethoxy* | Scheme 2 | 380/382 |

TABLE 1-continued

| # | R¹ | R² | R³ | method of preparation | M + H or m_p |
|---|---|---|---|---|---|
| 36 | pyrrolidinyl | piperazinyl | 1-(hydroxymethyl)cyclohexyl-amino | Scheme 1 | 447/449 |
| 37 | pyrrolidinyl | piperazinyl | (S)-1-hydroxybutan-2-ylamino | Scheme 1 | 407/409 |
| 38 | pyrrolidinyl | piperazinyl | (R)-1-hydroxybutan-2-ylamino | Scheme 1 | 407/409 |
| 39 | pyrrolidinyl | piperazinyl | (2S,3S)-3-hydroxybutan-2-yloxy | Scheme 2 | 408/410 |
| 40 | pyrrolidinyl | piperazinyl | (2R,3R)-3-hydroxybutan-2-yloxy | Scheme 2 | 408/410 |
| 41 | pyrrolidinyl | piperazinyl | (2S,3R)-3-hydroxybutan-2-yloxy | Scheme 2 | 408/410 |
| 42 | pyrrolidinyl | piperazinyl | (2R,3S)-3-hydroxybutan-2-yloxy | Scheme 2 | 408/410 |
| 43 | pyrrolidinyl | piperazinyl | 2-(hydroxymethyl)piperidin-1-yl | Scheme 3 | 433/435 |
| 44 | pyrrolidinyl | piperazinyl | 2-methylmorpholin-4-yl | Scheme 3 | 419/421 |
| 45 | pyrrolidinyl | piperazinyl | 2-phenylmorpholin-4-yl | Scheme 3 | 481/483 |
| 46 | pyrrolidinyl | piperazinyl | (3S)-3-hydroxypiperidin-1-yl | Scheme 3 | 419/421 |

TABLE 1-continued

| # | R¹ | R² | R³ | method of preparation | M + H or $m_p$ |
|---|---|---|---|---|---|
| 47 | *—N(pyrrolidine) | *—N(piperazine)NH | HO-azetidine-N-* | Scheme 3 | 391/393 |
| 48 | *—N(pyrrolidine) | *—N(piperazine)NH | (3R)-3-hydroxypiperidine-N-* | Scheme 3 | 419/421 |
| 49 | *—N(pyrrolidine) | *—N(piperazine)NH | (3R)-3-hydroxypyrrolidine-N-* | Scheme 3 | 405/407 |
| 50 | *—N(pyrrolidine) | *—N(piperazine)NH | (3S)-3-hydroxypyrrolidine-N-* | Scheme 3 | 405/407 |
| 51 | *—N(pyrrolidine) | *—N(piperazine)NH | tetrahydropyran-3-yloxy-* | Scheme 2 | 420/422 |
| 52 | *—N(pyrrolidine) | *—N(piperazine)NH | (3S)-tetrahydrofuran-3-ylmethoxy | Scheme 2 | 406/408 |
| 53 | *—N(pyrrolidine) | *—N(piperazine)NH | (3R)-tetrahydrofuran-3-ylmethoxy | Scheme 2 | 406/408 |
| 54 | *—N(thiomorpholine)S | *—N(piperazine)NH | morpholine-N-* | Scheme 3 | 437/439 |
| 55 | *—N(thiomorpholine)S | *—N(piperazine)NH | *-NH-CH(iPr)-CH2OH | Scheme 1 | 453/455 |
| 56 | *—N(thiomorpholine)S | *—N(piperazine)NH | (3S)-tetrahydrofuran-3-ylmethoxy | Scheme 2 | 438/440 |

TABLE 1-continued
| # | R¹ | R² | R³ | method of preparation | M + H or m_p |
|---|---|---|---|---|---|
| 57 | 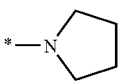 | 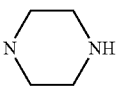 | 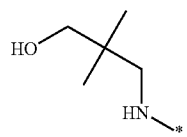 | Scheme 1 | 421/423 |
| 58 | 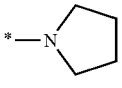 |  | 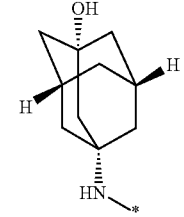 | Scheme 1 | 485/487 |
| 59 | 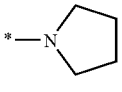 | 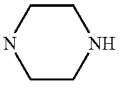 | 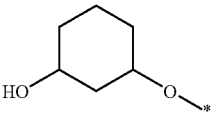 | Scheme 2 | 434/436 |
| 60 | 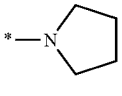 |  | 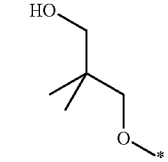 | Scheme 2 | 422/424 |
| 61 | 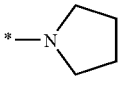 | 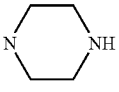 | 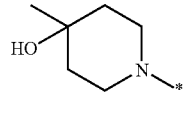 | Scheme 3 | 433/435 |
| 62 | 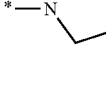 | 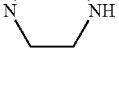 | 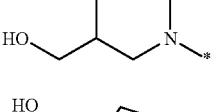 | Scheme 3 | 433/435 |
| 63 | 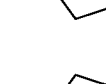 | 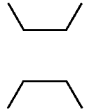 | 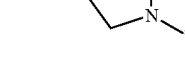 | Scheme 3 | 419/421 |
| 64 | 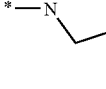 | 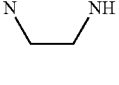 | 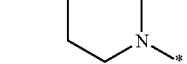 | Scheme 3 | 419/421 |
| 65 | 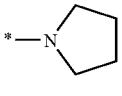 |  | 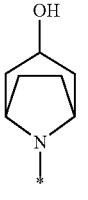 | Scheme 3 | 445/447 |
| 66 | 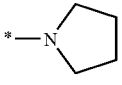 | 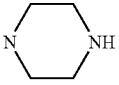 | 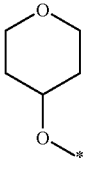 | Scheme 2 | 420/422 |

TABLE 1-continued

| # | R¹ | R² | R³ | method of preparation | M + H or $m_p$ |
|---|----|----|----|----|----|
| 67 | pyrrolidin-1-yl | piperazin-1-yl | tetrahydro-2H-pyran-4-ylamino | Scheme 1 | 419/421 |
| 68 | pyrrolidin-1-yl | piperazin-1-yl | 4-phenyltetrahydro-2H-pyran-4-yloxy | Scheme 2 | 496/498 |
| 69 | thiomorpholin-4-yl | piperazin-1-yl | tetrahydro-2H-pyran-4-yloxy | Scheme 2 | 452/454 |
| 70 | pyrrolidin-1-yl | piperazin-1-yl | 3-hydroxypropoxy | Scheme 2 | 394/396 |
| 71 | pyrrolidin-1-yl | piperazin-1-yl | 3-methoxypropoxy | Scheme 2 | 408/410 |
| 72 | pyrrolidin-1-yl | piperazin-1-yl | 3-hydroxy-3-methylbutoxy | Scheme 2 | 422/424 |
| 73 | pyrrolidin-1-yl | piperazin-1-yl | 2,3-dihydro-1H-inden-2-ylamino | Scheme 1 | 451/453 |
| 74 | pyrrolidin-1-yl | piperazin-1-yl | cyclopentylamino | Scheme 1 | 403/405 |

TABLE 1-continued

| # | R¹ | R² | R³ | method of preparation | M + H or $m_p$ |
|---|---|---|---|---|---|
| 75 | *—N(pyrrolidine) | *—N(piperazine)NH | ethyl piperidine-1-carboxylate, 4-NH—* | Scheme 1 | 490/492 |
| 76 | *—N(pyrrolidine) | *—N(piperazine)NH | cyclobutyl-NH—* | Scheme 1 | 389/391 |
| 77 | *—N(pyrrolidine) | *—N(piperazine)NH | *—NH-(3-phenylcyclopentyl) | Scheme 1 | 479/481 |
| 78 | *—N(pyrrolidine) | *—N(piperazine)NH | 4-hydroxycyclohexyl-NH—* | Scheme 1 | 433/435 |
| 79 | *—N(pyrrolidine) | *—N(piperazine)NH | norbornyl-NH—* | Scheme 1 | 429/431 |
| 80 | *—N(pyrrolidine) | *—N(piperazine)NH | cyclopropylmethyl-NH—* | Scheme 1 | 389/391 |
| 81 | *—N(pyrrolidine) | *—N(piperazine)NH | cyclopropylmethyl-O—* | Scheme 2 | 390/392 |
| 82 | *—N(pyrrolidine) | *—N(piperazine)NH | cyclobutyl-O—* | Scheme 2 | 390/392 |
| 83 | *—N(pyrrolidine) | *—N(piperazine)NH | cyclopropyl-NH—* | Scheme 1 | 375/377 |

TABLE 1-continued

| # | R¹ | R² | R³ | method of preparation | M + H or m$_p$ |
|---|---|---|---|---|---|
| 84 | *—N(pyrrolidine) | *—N(piperazine)NH | 2,3-dihydro-1H-inden-2-yloxy | Scheme 2 | m$_p$. 213/215' |
| 85 | *—N(pyrrolidine) | *—N(piperazine)NH | 1,2,3,4-tetrahydronaphthalen-2-yloxy | Scheme 2 | m$_p$. 187/189' |
| 86 | *—N(pyrrolidine) | *—N(piperazine)NH | adamantan-1-ylamino | Scheme 1 | 469/471 |
| 87 | *—N(pyrrolidine) | *—N(piperazine)NH | adamantan-2-ylamino | Scheme 1 | 469/471 |
| 88 | *—N(pyrrolidine) | *—N(piperazine)NH | chroman-4-yloxy | Scheme 2 | 468/470 |
| 89 | *—N(pyrrolidine) | *—N(piperazine)NH | 3,5-dichloropyridin-4-ylamino | Scheme 1 | 480/482/ 484/486 |
| 90 | *—N(pyrrolidine) | *—N(piperazine)NH | 1-(tetrahydro-2H-pyran-4-yl)piperidin-4-ylamino | Scheme 1 | 502/504 |
| 91 | *—N(pyrrolidine) | *—N(piperazine)NH | 4,5-dimethylthiazol-2-ylamino | Scheme 1 | 446/448 |
| 92 | *—N(pyrrolidine) | *—N(piperazine)NH | 5-methylthiazol-2-ylamino | Scheme 1 | 432/434 |
| 93 | *—N(pyrrolidine) | *—N(piperazine)NH | 4-tert-butylthiazol-2-ylamino | Scheme 1 | 474/476 |
| 94 | *—N(pyrrolidine) | *—N(piperazine)NH | 5-(hydroxymethyl)-4-methylthiazol-2-ylamino | Scheme 1 | 476/478 |

TABLE 1-continued

| # | R¹ | R² | R³ | method of preparation | M + H or $m_p$ |
|---|---|---|---|---|---|
| 95 | *—N(pyrrolidine) | *—N(piperazine)NH | 5-tert-butyl-thiazol-2-yl-NH—* | Scheme 1 | 474/476 |
| 96 | *—N(pyrrolidine) | *—N(piperazine)NH | 4-methyl-thiazol-2-yl-NH—* | Scheme 1 | 432/434 |
| 97 | *—N(pyrrolidine) | *—N(piperazine)NH | 5-methyl-1,3,4-thiadiazol-2-yl-NH—* | Scheme 1 | 433/435 |
| 98 | *—N(pyrrolidine) | *—N(piperazine)NH | 3-methyl-isothiazol-5-yl-NH—* | Scheme 1 | 432/434 |
| 99 | *—N(pyrrolidine) | *—N(piperazine)NH | *—NH₂ | Scheme 1 | 335/337 |
| 100 | *—N(pyrrolidine) | *—N(piperazine)NH | *—N(thiazolidine) | Scheme 3 | 407/409 |
| 101 | *—N(pyrrolidine) | *—N(piperazine)NH | 2-(pyridin-4-yl)pyrrolidin-1-yl—* | Scheme 3 | 446/448 |
| 102 | *—N(pyrrolidine) | *—N(piperazine)NH | *—N(4-phenylpiperazin-1-yl) | Scheme 3 | 480/482 |
| 103 | *—N(pyrrolidine) | *—N(piperazine)NH | *—O-ethyl | Scheme 2 | 364/366<br>178-180° C. |
| 104 | *—N(pyrrolidine) | *—N(piperazine)NH | *—O-CH₂-CHF₂ | Scheme 2 | 400/402<br>193-195° C. |
| 105 | *—N(pyrrolidine) | *—N(piperazine)NH | *—OH | Scheme 2 | 336/338 |
| 106 | *—N(pyrrolidine) | *—N(piperazine)NH | *—N(piperidin-3-yl-CH₂-morpholine) | Scheme 3 | 502/504 |

TABLE 1-continued

| # | R¹ | R² | R³ | method of preparation | M + H or $m_p$ |
|---|---|---|---|---|---|
| 107 | pyrrolidinyl | piperazinyl | (S)-2-methylpiperidinyl | Scheme 3 | 417/419 |
| 108 | pyrrolidinyl | piperazinyl | (R)-2-methylpiperidinyl | Scheme 3 | 417/419 |
| 109 | pyrrolidinyl | piperazinyl | (S)-2-cyclopropyl-2-hydroxyethylamino | Scheme 1 | 419/421 |
| 110 | pyrrolidinyl | piperazinyl | 2-(cyclopropylmethyl)-2-hydroxyethylamino | Scheme 1 | 433/435 |
| 111 | pyrrolidinyl | piperazinyl | 3-(hydroxymethyl)morpholinyl | Scheme 3 | 435/437 |
| 112 | pyrrolidinyl | piperazinyl | (S)-tetrahydropyran-3-yloxy | Scheme 2 | 420/422 |
| 113 | azetidinyl | piperazinyl | cyclobutylamino | Scheme 3 | 375/377 |
| 114 | azetidinyl | piperazinyl | tetrahydropyran-4-yloxy | Scheme 2 | 406/408 |
| 115 | azetidinyl | piperazinyl | (S)-tetrahydrofuran-3-yloxy | Scheme 2 | 392/394 |
| 116 | pyrrolidinyl | piperazinyl | (1-hydroxycyclohexyl)methylamino | Scheme 1 | 447/449 |

TABLE 1-continued

| # | R¹ | R² | R³ | method of preparation | M + H or m_p |
|---|---|---|---|---|---|
| 117 | 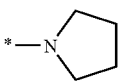 | 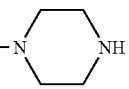 | 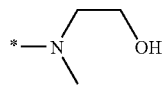 | Scheme 1 | 393/395 |

Indications

As has been found, the compounds of formula 1 are characterised by their wide range of applications in the therapeutic field. Particular mention should be made of those applications for which the compounds according to the invention of formula 1 are preferably suited on account of their pharmaceutical efficacy as PDE4 inhibitors. Examples include respiratory or gastrointestinal diseases or complaints, inflammatory diseases of the joints, skin or eyes, cancers, and also diseases of the peripheral or central nervous system.

Particular mention should be made of the prevention and treatment of diseases of the airways and of the lung which are accompanied by increased mucus production, inflammations and/or obstructive diseases of the airways. Examples include acute, allergic or chronic bronchitis, chronic obstructive bronchitis (COPD), coughing, pulmonary emphysema, allergic or non-allergic rhinitis or sinusitis, chronic rhinitis or sinusitis, asthma, alveolitis, Farmer's disease, hyperreactive airways, infectious bronchitis or pneumonitis, paediatric asthma, bronchiectases, pulmonary fibrosis, ARDS (acute adult respiratory distress syndrome), bronchial oedema, pulmonary oedema, bronchitis, pneumonia or interstitial pneumonia triggered by various causes, such as aspiration, inhalation of toxic gases, or bronchitis, pneumonia or interstitial pneumonia as a result of heart failure, irradiation, chemotherapy, pulmonary fibrosis or mucoviscidosis, or alpha1-antitrypsin deficiency.

Also deserving special mention is the treatment of inflammatory diseases of the gastrointestinal tract. Examples include acute or chronic inflammatory changes in gall bladder inflammation, Crohn's disease, ulcerative colitis, inflammatory pseudopolyps, juvenile polyps, colitis cystica profunda, pneumatosis cystoides intestinales, diseases of the bile duct and gall bladder, e.g. gallstones and conglomerates, for the treatment of inflammatory diseases of the joints such as rheumatoid arthritis or inflammatory diseases of the skin and eyes.

Preferential mention should also be made of the treatment of cancers. Examples include all forms of acute and chronic leukaemias such as acute lymphatic leukaemia (ALL) and acute myeloid leukaemia (AML), acute non-lymphocytic leukaemia (ANLL), chronic lymphatic leukaemia (CLL), chronic myeloid leukaemia (CML), hair cell leukaemia, acute promyelocytic leukaemia (APL), particularly the APL subform with a chromosomal t(15; 17) translocation, diseases of the lymphatic organs, Hodgkin's lymphomas and non-Hodgkin's lymphomas and bone tumours such as e.g. osteosarcoma and all kinds of gliomas such as e.g. oligodendroglioma and glioblastoma.

Preferential mention should also be made of the prevention and treatment of diseases of the peripheral or central nervous system. Examples of these include depression, bipolar or manic depression, acute and chronic anxiety states, schizophrenia, Alzheimer's disease, Parkinson's disease, acute and chronic multiple sclerosis or acute and chronic pain as well as injuries to the brain caused by stroke, hypoxia or craniocerebral trauma.

Particularly preferably the present invention relates to the use of compounds of formula 1 for preparing a pharmaceutical composition for the treatment of inflammatory or obstructive diseases of the upper and lower respiratory tract including the lungs, such as for example allergic rhinitis, chronic rhinitis, bronchiectasis, cystic fibrosis, idiopathic pulmonary fibrosis, fibrosing alveolitis, COPD, chronic bronchitis, chronic sinusitis, asthma, particularly COPD, chronic bronchitis and asthma.

It is most preferable to use the compounds of formula 1 for the treatment of inflammatory and obstructive diseases such as COPD, chronic bronchitis, chronic sinusitis, asthma, Crohn's disease, ulcerative colitis, particularly COPD, chronic bronchitis and asthma.

It is also preferable to use the compounds of formula 1 for the treatment of diseases of the peripheral or central nervous system such as depression, bipolar or manic depression, acute and chronic anxiety states, schizophrenia, Alzheimer's disease, Parkinson's disease, acute and chronic multiple sclerosis or acute and chronic pain as well as injuries to the brain caused by stroke, hypoxia or craniocerebral trauma.

An outstanding aspect of the present invention is the reduced profile of side effects. This means, within the scope of the invention, being able to administer a dose of a pharmaceutical composition without inducing vomiting, preferably nausea and most preferably malaise in the patient. It is particularly preferable to be able to administer a therapeutically effective quantity of substance without inducing emesis or nausea, at every stage of the disease.

Formulations

In another aspect the invention relates to medicaments for treating respiratory complaints which contain one or more of the above-mentioned pteridines of formula 1.

Suitable forms for administration are for example tablets, capsules, solutions, syrups, emulsions or inhalable powders or aerosols. The content of the pharmaceutically effective compound(s) in each case should be in the range from 0.1 to 90 wt. %, preferably 0.5 to 50 wt. % of the total composition, i.e. in amounts which are sufficient to achieve the dosage range specified hereinafter.

The preparations may be administered orally in the form of a tablet, as a powder, as a powder in a capsule (e.g. a hard gelatine capsule), as a solution or suspension. When administered by inhalation the active substance combination may be given as a powder, as an aqueous or aqueous-ethanolic solution or using a propellant gas formulation.

Preferably, therefore, pharmaceutical formulations are characterised in that they contain one or more compounds of formula 1 according to the preferred embodiments above.

It is particularly preferable if the compounds of formula 1 are administered orally, and it is also particularly preferable if they are administered once or twice a day. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

For oral administration the tablets may, of course, contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

It is also preferred if the compounds of formula 1 are administered by inhalation, particularly preferably if they are administered once or twice a day. For this purpose, the compounds of formula 1 have to be made available in forms suitable for inhalation. Inhalable preparations include inhalable powders, propellant-containing metered-dose aerosols or propellant-free inhalable solutions, which are optionally present in admixture with conventional physiologically acceptable excipients.

Within the scope of the present invention, the term propellant-free inhalable solutions also includes concentrates or sterile ready-to-use inhalable solutions. The preparations which may be used according to the invention are described in more detail in the next part of the specification.

Inhalable Powders

If the active substances of formula 1 are present in admixture with physiologically acceptable excipients, the following physiologically acceptable excipients may be used to prepare the inhalable powders according to the invention: monosaccharides (e.g. glucose or arabinose), disaccharides (e.g. lactose, saccharose, maltose), oligo- and polysaccharides (e.g. dextran), polyalcohols (e.g. sorbitol, mannitol, xylitol), salts (e.g. sodium chloride, calcium carbonate) or mixtures of these excipients with one another. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred. Methods of preparing the inhalable powders according to the invention by grinding and micronising and by finally mixing the components together are known from the prior art.

Propellant-Containing Inhalable Aerosols

The propellant-containing inhalable aerosols which may be used according to the invention may contain 1 dissolved in the propellant gas or in dispersed form. The propellant gases which may be used to prepare the inhalation aerosols according to the invention are known from the prior art. Suitable propellant gases are selected from among hydrocarbons such as n-propane, n-butane or isobutane and halohydrocarbons such as preferably fluorinated derivatives of methane, ethane, propane, butane, cyclopropane or cyclobutane. The propellant gases mentioned above may be used on their own or in mixtures thereof. Particularly preferred propellant gases are fluorinated alkane derivatives selected from TG134a (1,1,1,2-tetrafluoroethane), TG227 (1,1,1,2,3,3,3-heptafluoropropane) and mixtures thereof. The propellant-driven inhalation aerosols used within the scope of the use according to the invention may also contain other ingredients such as co-solvents, stabilisers, surfactants, antioxidants, lubricants and pH adjusters. All these ingredients are known in the art.

Propellant-Free Inhalable Solutions

The compounds of formula 1 according to the invention are preferably used to prepare propellant-free inhalable solutions and inhalable suspensions. Solvents used for this purpose include aqueous or alcoholic, preferably ethanolic solutions. The solvent may be water on its own or a mixture of water and ethanol. The solutions or suspensions are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulphuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc. Preferred inorganic acids are hydrochloric and sulphuric acids. It is also possible to use the acids which have already formed an acid addition salt with one of the active substances. Of the organic acids, ascorbic acid, fumaric acid and citric acid are preferred. If desired, mixtures of the above acids may also be used, particularly in the case of acids which have other properties in addition to their acidifying qualities, e.g. as flavourings, antioxidants or complexing agents, such as citric acid or ascorbic acid, for example. According to the invention, it is particularly preferred to use hydrochloric acid to adjust the pH.

Co-solvents and/or other excipients may be added to the propellant-free inhalable solutions used for the purpose according to the invention. Preferred co-solvents are those which contain hydroxyl groups or other polar groups, e.g. alcohols—particularly isopropyl alcohol, glycols—particularly propyleneglycol, polyethyleneglycol, polypropyleneglycol, glycolether, glycerol, polyoxyethylene alcohols and polyoxyethylene fatty acid esters. The terms excipients and additives in this context denote any pharmacologically acceptable substance which is not an active substance but which can be formulated with the active substance or substances in the pharmacologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilisers, complexing agents, antioxidants and/or preservatives which guarantee or prolong the shelf life of the finished pharmaceutical formulation, flavourings, vitamins and/or other additives known in the art. The additives also include pharmacologically acceptable salts such as sodium chloride as isotonic agents. The preferred excipients include antioxidants such as ascorbic acid, for example, provided that it has not already been used to adjust the pH, vitamin A, vitamin E, tocopherols and similar vitamins or provitamins occurring in the human body. Preservatives may be used to protect the formulation from contamination with pathogens. Suitable preservatives are those which are known in the art, particularly cetyl pyridinium chloride, benzalkonium chloride or benzoic acid or benzoates such as sodium benzoate in the concentration known from the prior art.

For the treatment forms described above, ready-to-use packs of a medicament for the treatment of respiratory complaints are provided, containing an enclosed description including for example the words respiratory disease, COPD or asthma, and a pteridine of formula 1.

We claim:

1. A method of treating chronic obstructive pulmonary disease (COPD) or asthma, the method comprising administering to a patient in need thereof a therapeutically effective amount of a compound of formula 1,

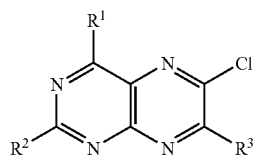

wherein:
$R^1$ is pyrrolidinyl;
$R^2$ is piperazinyl; and
$R^3$ is $NHR^{3.1}$ or $OR^{3.1}$, wherein $R^{3.1}$ is H or a group selected from branched or unbranched alkyl with 1 to 6 carbon atoms substituted by one or more hydroxyl groups, $C_{1-6}$-haloalkyl, $C_{1-6}$-alkylene-O—$C_{1-2}$-alkyl, a mono- or bicyclic, saturated or partially unsaturated $C_{3-10}$-cycloalkyl, mono- or bicyclic, saturated or partially saturated, four-to ten-membered heterocyclic group with 1 to 3 heteroatoms selected from S, N, or O, and a mono- or bicyclic, five- to ten-membered heteroaromatic group with 1 to 4 heteroatoms selected from S, N, or O, which may optionally be substituted by one or more groups selected from among OH, halogen, $C_{1-6}$-alkyl, branched or unbranched alkyl with 1 to 6 carbon atoms substituted by one or more hydroxyl groups, $C_{1-6}$-haloalkyl, $COOR^{3.3}$, O—$C_{1-6}$-alkyl, $C_{6-10}$-aryl, $C_{3-10}$-cycloalkyl, four- to ten-membered heterocyclic group, five- to ten-membered heteroaromatic group, and O—$C_{1-4}$-alkyl-henyl, wherein this group is optionally substituted by one or more groups selected from halogen, OH, $C_{1-3}$-alkyl, and $C_{1-3}$-haloalkyl, and wherein $R^{3.3}$ is H, $C_{1-6}$-alkyl, or branched or unbranched alkyl with 1 to 6 carbon atoms substituted by one or more hydroxyl groups, or $R^3$ is a saturated or partially saturated, bi- or polycyclic seven-, eight-, nine-, or ten-membered heterocyclic group containing a nitrogen atom and optionally containing one, two, or three other atoms selected from S, N, and O and which are optionally substituted by one or more groups selected from OH, halogen, $C_{1-6}$-alkyl, branched or unbranched alkyl with 1 to 6 carbon atoms substituted by one or more hydroxyl groups, $C_{1-4}$-alkyl-O—$C_{1-3}$-alkyl, $C_{6-10}$-aryl, $C_{3-10}$-cycloalkyl, five- to ten-membered heteroaryl, four- to ten-membered heterocyclic group, $C_{1-2}$-alkylene-$C_{5-10}$-heteroaryl, and $C_{1-2}$-alkylene-$C_{4-10}$ heterocycle, each of which are optionally substituted by one or more groups selected from methyl, ethyl, O-methyl, Cl, F, and OH, and the pharmacologically acceptable salts, diastereomers, enantiomers, and racemates thereof.

2. The method according to claim 1, wherein:
$R^1$ is pyrrolidinyl;
$R^2$ is piperazinyl; and
$R^3$ is $NHR^{3.1}$ or $OR^{3.1}$, wherein $R^{3.1}$ is H or a group selected from branched or unbranched alkyl with 1 to 6 carbon atoms substituted by one or more hydroxyl groups, $C_{1-6}$-haloalkyl, $C_{1-6}$-alkylene-O—$C_{1-2}$-alkyl, mono- or bicyclic, saturated or partially unsaturated $C_{3-10}$-cycloalkyl, mono- or bicyclic, saturated or partially saturated, four-to ten-membered heterocyclic group with 1 or 2 heteroatoms selected from S, N, or O, and a mono- or bicyclic, five- to ten-membered heteroaromatic group with 1, 2 or 3 heteroatoms selected from S, N, or O optionally substituted by one or more groups selected from OH, $C_{1-6}$-alkyl, branched or unbranched alkyl with 1 to 6 carbon atoms substituted by one or more hydroxyl groups, COO—$C_{1-3}$-alkyl, O—$C_{1-3}$-alkyl, phenyl, $C_{3-10}$-cycloalkyl, four-to ten-membered heterocyclic group, five- to ten-membered heteroaromatic group, and O—$CH_2$-phenyl, each of which are optionally substituted by at least one group selected from halogen, OH, $C_{1-3}$-alkyl, and $C_{1-3}$-haloalkyl, or $R^3$ is a saturated or partially saturated, bi- or polycyclic seven-, eight-, nine-, or ten-membered heterocyclic group containing a nitrogen atom and optionally containing one, two, or three other atoms selected from S, N, and O and optionally substituted by one or more groups selected from OH, $C_{1-6}$-alkyl, branched or unbranched alkyl with 1 to 6 carbon atoms substituted by one or more hydroxyl groups, $CH_2$-O—$CH_3$, phenyl, $C_{3-10}$-cycloalkyl, five- to ten-membered heteroaryl, four- to ten-membered heterocyclic group, $CH_2$-$C_{5-10}$-heteroaryl, and $CH_2$-$C_{4-10}$ heterocycle, each of which are optionally substituted by one or more groups selected from methyl, O-methyl, Cl, and OH, and the pharmacologically acceptable salts, diastereomers, enantiomers, or racemates thereof.

3. The method according to claim 1, wherein:
$R^3$ is a saturated or partially saturated, bi- or polycyclic seven-, eight-, nine-, or ten-membered heterocyclic group containing a nitrogen atom and linked to the rest of the molecule via this nitrogen atom and which optionally contains one, two, or three other atoms selected from S, N, and O and which optionally substituted by one or more groups selected from OH, (halogen), $C_{1-6}$-alkyl, branched or unbranched alkyl with 1 to 6 carbon atoms substituted by one or more hydroxyl groups, $C_{1-4}$-alkyl-O—$C_{1-3}$-alkyl, $C_{6-10}$-aryl, $C_{3-10}$-cycloalkyl, five- to ten-membered heteroaryl, four- to ten-membered heterocyclic group, $C_{1-2}$-alkylene-$C_{5-10}$-heteroaryl, and $C_{1-2}$-alkylene-$C_{4-10}$ heterocycle, which are optionally substituted by one or more groups selected from methyl, ethyl, O-methyl, Cl, F, and OH, and the pharmacologically acceptable salts, diastereomers, enantiomers, or racemates thereof.

* * * * *